(12) United States Patent
Amies et al.

(10) Patent No.: US 12,214,220 B2
(45) Date of Patent: Feb. 4, 2025

(54) METHOD FOR PROVIDING RESULT DATA WHICH IS SUITABLE FOR USE IN PLANNING THE IRRADIATION OF A PATIENT

(71) Applicant: Siemens Healthcare GmbH, Erlangen (DE)

(72) Inventors: Christopher Jude Amies, Sykesville, MD (US); Christian Hofmann, Erlangen (DE); Philipp Hoelzer, Bubenreuth (DE); Mark-Aleksi Keller-Reichenbecher, Sandhausen (DE); Bjoern Kreisler, Hausen (DE); Andre Ritter, Neunkirchen am Brand (DE); Rene Kartmann, Nuremberg (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/502,308

(22) Filed: Nov. 6, 2023

(65) Prior Publication Data

US 2024/0066320 A1 Feb. 29, 2024

Related U.S. Application Data

(63) Continuation of application No. 17/123,594, filed on Dec. 16, 2020, now Pat. No. 11,844,961, which is a
(Continued)

(51) Int. Cl.
*A61N 5/10* (2006.01)

(52) U.S. Cl.
CPC ......... *A61N 5/1031* (2013.01); *A61N 5/1039* (2013.01); *A61N 5/1071* (2013.01); *A61N 2005/1061* (2013.01)

(58) Field of Classification Search
None
See application file for complete search history.

(56) References Cited

U.S. PATENT DOCUMENTS

| | | | |
|---|---|---|---|
| 2005/0105687 | A1 | 5/2005 | Heismann et al. |
| 2006/0034418 | A1 | 2/2006 | Heismann et al. |

(Continued)

FOREIGN PATENT DOCUMENTS

| | | |
|---|---|---|
| CN | 1737549 A | 2/2006 |
| CN | 102098963 A | 6/2011 |

(Continued)

OTHER PUBLICATIONS

International Search Report and Written Opinion issued Jan. 29, 2019 in International Application No. PCT/EP2018/069777.
(Continued)

*Primary Examiner* — Hoon K Song
(74) *Attorney, Agent, or Firm* — Harness, Dickey & Pierce, P.L.C.

(57) ABSTRACT

Computed tomography (CT) measurement data of the patient is acquired using a CT device having a quantum counting X-ray detector, and the CT measurement data is processed to generate result data, considering a specific information content of the CT measurement data resulting from the use of the quantum counting X-ray detector in acquiring the CT measurement data. The result data is suitable for use in the planning of irradiation of the patient. The result data is provisioned to an interface such that the result data is usable for planning the irradiation of the patient.

16 Claims, 8 Drawing Sheets

Related U.S. Application Data continuation of application No. 16/640,960, filed as application No. PCT/EP2018/069777 on Jul. 20, 2018, now Pat. No. 10,898,727.

(60) Provisional application No. 62/549,175, filed on Aug. 23, 2017.

(56) References Cited

U.S. PATENT DOCUMENTS

| | | |
|---|---|---|
| 2006/0104414 A1 | 5/2006 | Mayo |
| 2007/0153969 A1 | 7/2007 | Maschke |
| 2007/0164225 A1 | 7/2007 | Pang et al. |
| 2008/0210877 A1 | 9/2008 | Altman et al. |
| 2009/0122952 A1 | 5/2009 | Nishide et al. |
| 2010/0246915 A1 | 9/2010 | Yamakoshi et al. |
| 2011/0097273 A1 | 4/2011 | Proksa |
| 2012/0326049 A1 | 12/2012 | Hannemann et al. |
| 2013/0101082 A1 | 4/2013 | Jordan et al. |
| 2013/0329856 A1* | 12/2013 | Kuwahara ............ A61B 6/4241 378/62 |
| 2014/0254898 A1 | 9/2014 | Wang et al. |
| 2016/0016009 A1 | 1/2016 | Manzke et al. |
| 2016/0374635 A1 | 12/2016 | Ning et al. |
| 2017/0071559 A1 | 3/2017 | Kappler et al. |
| 2017/0113065 A1 | 4/2017 | Inaniwa et al. |
| 2017/0119340 A1 | 5/2017 | Nakai et al. |
| 2017/0337713 A1* | 11/2017 | Hoelzer ............ G06T 11/003 |
| 2018/0099152 A1 | 4/2018 | Nioutsikou |

FOREIGN PATENT DOCUMENTS

| | | |
|---|---|---|
| CN | 102841367 A | 12/2012 |
| CN | 103393408 A | 11/2013 |
| CN | 105120755 A | 12/2015 |
| DE | 102005059210 A1 | 6/2007 |
| DE | 102006026945 A1 | 12/2007 |
| DE | 102009032252 B3 | 8/2010 |
| DE | 102007034982 B4 | 7/2016 |
| EP | 1489969 B1 | 1/2007 |
| EP | 1876955 B1 | 11/2016 |
| EP | 3238780 A2 | 11/2017 |
| JP | 2010246883 A | 11/2010 |
| JP | 2011010885 A | 1/2011 |
| JP | 2011217805 A | 11/2011 |
| JP | 2014174174 A | 9/2014 |
| JP | 2016000118 A | 1/2016 |
| JP | 2017086872 A | 5/2017 |
| WO | WO-03/065077 A2 | 8/2003 |

OTHER PUBLICATIONS

International Preliminary Report on Patentability Chapter I issued Feb. 25, 2020 in International Application No. PCT/EP2018/069777.

Notice of Allowance issued Sep. 17, 2020 in U.S. Appl. No. 16/640,960.

First Office Action issued Apr. 7, 2021 in Chinese Application No. 201880067153.4.

* cited by examiner

METHOD FOR PROVIDING RESULT DATA WHICH IS SUITABLE FOR USE IN PLANNING THE IRRADIATION OF A PATIENT

CROSS-REFERENCE TO RELATED APPLICATIONS

This application is a Continuation of U.S. application Ser. No. 17/123,594, filed on Dec. 16, 2020, which is a continuation of U.S. application Ser. No. 16/640,960, filed on Feb. 21, 2020, which is the National Phase under 35 U.S.C. § 371 of PCT International Application No. PCT/EP2018/069777, which has an international filing date of Jul. 20, 2018, which designated the United States of America and which claims priority to U.S. Provisional application 62/549,175, filed Aug. 23, 2017, the disclosures of each of which are hereby incorporated by reference in their entirety.

FIELD

Embodiments of the invention generally relate to a method for the provision of result data, which is suitable for use in planning an irradiation of a patient, an arithmetic unit, a CT device and a computer program product.

BACKGROUND

In radiotherapy, a target volume, for example, a tumor, of a patient is irradiated with ionizing radiation. In this case, external radiotherapy, which comprises the irradiation of a body of the patient from outside the body, is known. Likewise, internal radiotherapy, also referred to as brachytherapy, is known. In brachytherapy, radiation sources comprising radioactive substances are introduced into a body of the patient to locally damage or destroy the tumor tissue in the target volume in the body of the patient.

In principle, during irradiation of the patient it is a challenge to ensure that a sufficient radiation dose is supplied to a target volume such that the tumor tissue contained in the target volume is destroyed. At the same time, organs at risk, which surround the target volume and form at least one risk volume, should be spared as much as possible. A high degree of accuracy during the planning and/or preparation of the irradiation is therefore of great importance.

It is known to plan and/or to prepare for radiotherapy and/or irradiation of a patient by imaging. An irradiation plan is customarily produced for this purpose with the aid of medical measurement data of the patient produced using a three-dimensional imaging method. Customarily, computer tomography measurement data (CT measurement data) acquired via a computer tomography device (CT device) is used for this. Using the computer tomography measurement data, on the one hand the target volume of irradiation can be established, and on the other hand, the surrounding risk volume located. Furthermore, the intensity values of the CT measurement data (measured in so-called "Hounsfield Units") depict an electron density in a good approximation at the corresponding location in the body of the patient as the intensity values are based on the absorption of the X-rays at the associated locations. In this way, the CT measurement data can be converted particularly easily into an electron density map for the planning of irradiation. As the intensity of the interaction of the radiation correlates with the electron density in the body during irradiation, it is comparatively easy to calculate the attenuation of the radiation as it passes through the body of the patient from the CT measurement data. Furthermore, CT measurement data only displays slight geometric distortion and thus enables a suitable definition of a reference geometry for the planning of irradiation and the performance of irradiation. Based on this property, CT measurement data has hitherto been used preferably in the planning of irradiation.

In recent times, besides the conventional detector types with integral detector elements used hitherto, such quantum counting X-ray detector have been proposed for use in CT devices. For example, a CT device is known from EP 1489969 B1, the detectors of which can detect X-ray radiation received by the detectors with regard to the number of X-ray quanta, the quantum energy of which exceeds a predetermined threshold value. A method for operating a quantum counting X-ray detector is described in DE 10 2007 034 982 B4. A method for generating energy-selective X-ray images of a field of view is known from DE 10 2009 032 252 B3.

SUMMARY

A quantum counting X-ray detector, also referred to as a direct-converting X-ray detector or photon-counting X-ray detector, enables the direct conversion of a high-energy photon into electron-hole pairs when the high-energy photon impinges on a semiconductor material of the quantum counting X-ray detector. The electrons generated in the semiconductor material can subsequently be converted into an electrical signal pulse in an integrated circuit. A pulse height of the signal pulse can correlate with the energy of the high-energy photon. By establishing suitable energy thresholds, individual detected high-energy photons can thus be counted in different energy bands.

In the field of computer tomography, the use of quantum counting X-ray detector enables various advantages. Thus, the CT measurement data acquired by the CT device can have an intrinsic spectral sensitivity as the energy of the detected photons, as explained in the previous section, can be directly detected. Furthermore, the CT measurement data acquired by the CT device has an intrinsic high resolution as the detector elements of the quantum counting X-ray detector are typically smaller than the detector elements of conventional X-ray detectors. Furthermore, quantum counting X-ray detector customarily perform well at low signal intensity as typically electronic noise is almost completely suppressed as the electronic noise is below the first energy threshold set. Furthermore, the counting of individual photons enables the reduction of an inherent energy weighting of the quantum counting X-ray detector.

At least one embodiment is directed to a method for the provision of result data, which is particularly suitable for use in a planning of an irradiation of a patient.

The method, according to at least one embodiment, for the provision of result data which is suitable for use in a planning of an irradiation of a patient comprises:

The acquisition of CT measurement data of the patient, which has been acquired by a CT device having a quantum counting X-ray detector, The processing of the CT measurement data, wherein the specific information content of the CT measurement data resulting from the use of the quantum counting X-ray detector in the acquisition of the CT measurement data is considered when processing the CT measurement data, wherein result data which is suitable for use in the planning of irradiation of the patient is generated when processing the CT measurement data, The provision of the result data to an interface such that the result data can be used for the planning of irradiation of the patient.

In general, the use of a quantum counting X-ray detector can enable the acquisition of CT measurement data, which is particularly suitable for use in the planning of the irradiation of the patient. Furthermore, by suitable processing of the acquired CT measurement data, which is particularly advantageously matched to the specific information content of the CT measurement data, result data can be generated which is particularly suitable for use in the planning of the irradiation of the patient.

Various requirements can be imposed on CT measurement data and/or on result data processed from the CT measurement data so that this data is particularly suitable for use in the planning of the irradiation of the patient:

It can be advantageous that the CT measurement data has a high resolution and/or a high soft tissue contrast (with or without contrast media) so that a target volume and/or risk volume can be identified and differentiated for irradiation as precisely as possible in the processing of the CT measurement data. Furthermore, this requirement can also be decisive where movement of the organs of the patient occurs, for example, in the region of the thorax, abdomen or pelvis. The CT measurement data should in particular be suitable for the identification of organ boundaries of the organs which, for example, takes place via manual, semi-automatic or automatic contouring and/or segmentation. Thus, for example, a differentiation between muscle tissue and adipose tissue or between gray and white matter may be necessary when processing the CT measurement data. Furthermore, functional CT measurement data such as, for example, perfusion measurement data or ventilation measurement data, can be used advantageously for contouring the target volume and/or risk volume.

For dose calculation in the planning of irradiation, particularly in particle therapy with protons or carbon ions, it is particularly important that, in the processing of the CT measurement data, quantitative material coefficients such as, for example, an electron density and/or a mass density and/or an effective atomic number and/or a stopping power can be reliably derived from the CT measurement data. The quantitative material coefficients can then serve as a basis for a dose calculation for the planning of the irradiation of the patient. In particular, in the case of particle therapy, the irradiation of the patient with ionized particles, it is advantageous that the stopping power and/or the corresponding water equivalent path length (WEPL) is calculated on the basis of the CT measurement data. The use of the quantum counting X-ray detector also enables the acquisition of a normalizing image for each CT measurement data acquisition such that a calculation of the quantitative material coefficient can be performed in a normalized manner for contouring or dose calculation.

In the preparation of irradiation or during irradiation, CT measurement data, in particular, cone beam CT measurement data, which is acquired via a quantum counting flat-panel detector, can be used particularly advantageously for tracking of the target volume and/or the risk volume. The CT measurement data acquired via the quantum counting X-ray detector can then be used particularly advantageously to verify the positioning of the patient, in particular, the target volume, for irradiation. Likewise, the performance of online dosimetry is conceivable.

Finally, CT measurement data can be used particularly advantageously for monitoring a course of treatment, for example, for follow-up examinations. Thus, a reaction of the tissue to the irradiation, for example, in the form of an inflammation, a tumor regression or tumor progression, can be monitored via the CT measurement data. Accordingly, irradiation parameters for the irradiation of the patient can subsequently be suitably adapted within the meaning of adaptive irradiation. A response by the patient to the irradiation can also be examined by an evaluation of tumor parameters such as, for example, tumor size and/or tumor volume and/or angiogenesis, and by comparing these tumor parameters with previous measurements. The CT measurement data acquired via the quantum counting X-ray detector, together with the recognition of specific image features, for example, texture parameters, can be used in a particularly suitable manner in the target volume and/or risk volume to support or enable the taking of treatment decisions for the patient.

Hereinafter a description is to be provided of how CT measurement data can be acquired via the use of the quantum counting X-ray detector, which can at least partially meet the aforementioned requirements in a particularly suitable manner. A particularly suitable processing of the CT measurement data for use in the planning of the irradiation of the patient is also to be examined.

The CT device can be a typical CT device, which is used for the acquisition of planning image data for the planning of irradiation of the patient. In this case, the CT measurement data is customarily acquired before the start of the initial irradiation of the patient. The irradiation of the patient then customarily takes place at least one day after the acquisition of the CT measurement data. Furthermore, in this case the CT device is typically positioned in an examination room, which is spatially separated from a treatment room in which the irradiation of the patient takes place via the radiotherapy device.

However, it is also conceivable that the CT device is installed in the treatment room, in particular a radiation booth, in which the irradiation of the patient takes place via the radiotherapy device, together with the radiotherapy device. The CT device can then constitute part of the radiotherapy device or be installed separately from the radiotherapy device. The patient support device can go backwards and forwards between the radiotherapy device and the CT device. In the case described in this paragraph, the acquired CT measurement data can be used particularly advantageously for the adaptive planning of the irradiation of the patient, in particular for an adaptation of an already existing irradiation plan, and/or for a verification of a positioning of the patient for irradiation.

In special cases, it is also conceivable that the CT device has a C-arm, wherein the X-ray source and the at least one quantum counting X-ray detector are attached at opposite ends of the C-arm.

CT measurement data is in particular projection data acquired via the CT device or image data reconstructed from the projection data. The acquisition of the CT measurement data may comprise loading the CT measurement data acquired via the quantum counting X-ray detector from a database. The acquisition of the CT measurement data may also comprise the acquisition of the CT measurement data via the quantum counting X-ray detector.

The CT measurement data which has been acquired via the quantum counting X-ray detector may also be cone beam CT measurement data (CBCT measurement data). The CBCT measurement data is acquired in particular when the patient is already positioned on a patient support device of the radiotherapy device for irradiation by the radiotherapy device. The CBCT measurement data is acquired in particular when the patient is positioned in such a way that he need no longer be rearranged for irradiation by the radiotherapy device. The CBCT measurement data is acquired in particular immediately before the start of the irradiation of the patient or when the irradiation of the patient has already started. In this case, in particular an imaging device of the radiotherapy device has the quantum counting X-ray detector. In this case, the CBCT measurement data acquired in this way can be acquired for different advantageous applications within the framework of the planning and/or preparation of the irradiation of the patient:

For adaptive planning of the irradiation of the patient, in particular for adapting an existing irradiation plan,
For online dosimetry,
For verification of a positioning of the patient for irradiation,
For monitoring of the target volume and/or risk volume during the performance of the irradiation of the patient, in particular during a respiratory motion of the patient.

The CBCT measurement data can be used for one or any combination of the aforementioned applications.

In the event of the use of the CBCT measurement data acquired via the quantum counting X-ray detector for online dosimetry, an increase in the accuracy of the radiation dose supplied to the patient is conceivable. In particular, a direct calculation of the radiation dose from the CBCT measurement data is conceivable. In this way, it is possible to dispense with model-based methods for dose calculation. The quantum counting X-ray detector can advantageously detect small differences in the level of the radiation dose, which is supplied to different organs of the patient, for example, the lungs or bones.

The processing of the CT measurement data takes place in particular by a processing algorithm, wherein the CT measurement data is included as input parameters in the processing algorithm. The output parameters of the processing algorithm are generated, in particular, the result data. The processing of the CT measurement data comprises in particular at least one such processing step that is generated from the CT measurement data result data, which is suitable for use in the planning of the irradiation of the patient. In this way, the processing of the CT measurement data can comprise the conversion of the CT measurement data, for example, into a spatially resolved distribution of a material coefficient. The processing of the CT measurement data can also comprise the contouring and/or segmentation of an organ structure, in particular of the target volume and/or risk volume in the CT measurement data. Of course, further possibilities for processing the CT measurement data are conceivable. Various possibilities for processing the CT measurement data are described in the description of the embodiments.

The specific information content of the CT measurement data results from the use of the quantum counting X-ray detector for the acquisition of the CT measurement data. Thus, the specific information content of the CT measurement data can, for example, be a spectral resolution of the CT measurement data resulting from the inherent energy sensitivity of the quantum counting X-ray detector. It is also conceivable that the specific information content is a particularly high spatial resolution of the CT measurement data resulting from the use of the quantum counting X-ray detector for the acquisition of the CT measurement data. In principle, the use of the quantum counting X-ray detector can also simplify the processing of the CT measurement data such that suitable result data is generated particularly easily from the CT measurement data. Then the specific information content of the CT measurement data lies in the particular suitability of the CT measurement data for processing into result data, which is suitable for use in the planning of the irradiation of the patient. The specific information content of the CT measurement data can also result from the especially skillful acquisition of the CT measurement data, which is only possible as a result of the use of the quantum counting X-ray detector.

The specific information content of the CT measurement data is in particular taken into consideration in the processing of the CT measurement data such that particularly simple and/or efficient processing of the CT measurement data for generation of the result data is enabled. The specific information content of the CT measurement data can also enable the suitable processing of the CT measurement data in the first place.

Result data which is particularly suitable for use in the planning of the irradiation of the patient can thus be generated by the processing of the CT measurement data. The result data can take various forms, for example, it can be available in the form of a spatially resolved distribution of a material coefficient or a contour of an organ structure. In principle, the result data constitutes suitable input parameters for an irradiation planning algorithm by which an irradiation plan can be drawn up for the irradiation of the patient. Of course, besides the result data, other data can be included as input parameters in the irradiation planning algorithm. The CT measurement data acquired by the quantum counting X-ray detector can, for example, together with measurement data from other imaging modalities, for example, MR measurement data or PET measurement data, be included in the planning of the irradiation of the patient.

The irradiation planning algorithm can, in particular, access the interface, in particular the result data provided to the interface, to perform the actual planning of the irradiation of the patient. The planning of the irradiation of the patient is thus, as described in the following embodiment, a particularly advantageous, in particular downstream step of the method according to at least one embodiment of the invention.

At least one embodiment provides that the method comprises the following additional step: the performance of the planning of the irradiation of the patient, wherein the result data is retrieved from the interface and is used for the planning of the irradiation of the patient.

In this case, the irradiation planning algorithm in particular accesses the result data stored in the interface in order to retrieve and use this in the planning of the irradiation of the patient. For example, the result data may constitute the spatially resolved distribution of a material coefficient, which can be used as input parameters for a dose calculation irradiation planning algorithm. According to a further possibility, the result data comprises the contouring of a target volume and/or risk volume, which can be used as the basis for the planning of the irradiation. The result data can, of course, also be included in the planning of the irradiation in a way which otherwise appears expedient to a person skilled in the art.

At least one embodiment provides that the acquisition of the CT measurement data comprises the acquisition of spectrally resolved CT measurement data resulting from acquisition by the quantum counting X-ray detector, the processing of the CT measurement data comprises a calculation of a spatially resolved distribution of a quantitative material coefficient from the spectrally resolved CT measurement data and the provision of the result data comprises the provision of the spatially resolved distribution of the quantitative material coefficient to the interface.

The quantitative material coefficient in particular characterizes a physical property of the tissue. Accordingly, the quantitative material coefficient customarily has a physical unit. The quantitative material coefficient is calculated in particular for each voxel of the CT measurement data. The quantitative material coefficient can be selected from the following list: an electron density, a mass density, an effective atomic number, a linear attenuation coefficient for a certain energy or for a spectrum comprising a plurality of energies, a stopping power, a water equivalent path length (WEPL), a quantitative elemental composition of the tissue. Of course, a plurality of quantitative material coefficients constituting an arbitrary selection from this list can also be calculated. In addition, of course, further quantitative material coefficients, which appear expedient to a person skilled in the art are conceivable.

The spatially resolved distribution of the quantitative material coefficient can be calculated particularly suitably from the CT measurement data acquired by the quantum counting X-ray detector. A reason for this is, in particular, that the CT measurement data can be spectrally resolved due to acquisition by the quantum counting X-ray detector. This means, in particular, that for the acquisition of the CT measurement data from the quantum counting X-ray detector and the X-ray tubes of the CT device, there is a suitable configuration for acquiring CT measurement data for at least two different energy spectra. Due to the inherent energy resolution, the quantitative material coefficient can also be calculated retrospectively from spectrally resolved CT measurement data originally acquired for another purpose by the quantum counting X-ray detector. This procedure is described in more detail in one or more of the following embodiments.

The use of spectrally resolved CT measurement data for the calculation of the quantitative material coefficient is advantageously compared with the use of conventional CT measurement data, which is only available for an individual energy and/or an individual energy spectrum. The quantitative material coefficient can namely be calculated in particular directly from the spectrally resolved CT measurement data. In particular, only the spectrally resolved CT measurement data can then be included in the calculation of the spatially resolved distribution of the quantitative material coefficient.

In contrast, the quantitative material coefficient can typically only be calculated indirectly from the conventional CT measurement data. For typically the Hounsfield values (HU values) of the conventional CT measurement data cannot be used directly for the calculation of the quantitative material coefficient as they do not comprise any spectrally resolved energy information, but the attenuation in a given material is customarily a function of the energy. In order to enable the quantitative material coefficient to be calculated from conventional CT measurement data, typically a calibration measurement and storage of a conversion rule in a look-up table is therefore necessary. It follows from this that for conventional CT acquisition, limitations must customarily be implemented, for example, the tube voltage may not be altered.

These disadvantages can be addressed in a particularly suitable manner through the use of the quantum counting X-ray detector for the acquisition of the spectrally resolved CT measurement data because due to the energy resolution, the spectrally resolved CT measurement data can advantageously be directly included in the calculation of the quantitative material coefficient. Thus, the calibration measurement, which is customarily necessary for the conventional CT measurement data, can be advantageously omitted. Furthermore, limitations in the acquisition of the spectrally resolved CT measurement data can be advantageously omitted.

In addition, the quality and/or accuracy of the quantitative material coefficient reconstructed from the spectrally resolved CT measurement data is advantageously higher than from conventional CT measurement data. Reasons for this are, for example, that dependence on the calibration measurement and thus on the acquisition parameters selected in the acquisition can be omitted. In addition, dependence on an elemental composition of the tissue, which possibly influences the conversion rule ascertained in calibration, can be omitted.

Furthermore, the spectrally resolved CT measurement data can be acquired in an optimized manner for additional tasks by the quantum counting X-ray detector, for example, particularly optimized for subsequent contouring of the target volume and/or risk volume. For example, a particularly suitable contrast-to-noise ratio (CNR) can be ensured in the spectrally resolved CT measurement data such that, in addition to the calculation of the quantitative material coefficient, the spectrally resolved CT measurement data is also particularly suitable for contouring. It is advantageously unnecessary to establish which quantitative material coefficient should be reconstructed from the spectrally resolved CT measurement data in the run-up to acquisition of the spectrally resolved CT measurement data. Ideally, it is unnecessary to adapt acquisition parameters to the acquisition of spectrally resolved CT measurement data so that the quantitative material coefficient can be reconstructed from the spectrally resolved CT measurement data. Furthermore, it is conceivable that different quantitative material coefficients are reconstructed from the spectrally resolved CT measurement data.

The spatially resolved distribution of the quantitative material coefficient is in particular provided for a dose calculation algorithm. Of course, other applications of the quantitative material coefficient are also conceivable with regard to the planning of the irradiation of the patient.

A standardized acquisition protocol is advantageously defined for the acquisition of the spectrally resolved CT measurement data. The quantitative material coefficient can thus be advantageously reconstructed in a standardized manner directly from the spectrally resolved CT measurement data. The standardized acquisition protocol comprises, for example, standardized energy thresholds, which are particularly suitable for the calculation of the quantitative material coefficient, for example, the electron density. Furthermore, the standardized acquisition of the spectrally resolved CT measurement data can facilitate the processing of the spatially resolved distribution of a quantitative material coefficient from the spectrally resolved CT measurement data. For example, a standardized calculation of spatially resolved distributions of two different quantitative material coefficients from the spectrally resolved CT measurement data is particularly advantageous. These two-parameter models can provide a particularly suitable basis for the planning of the irradiation of the patient. This procedure is described in more detail in one or more of the following embodiments.

The quantitative material coefficient calculated by the CT measurement data can also be used in a suitable manner for radiomics studies and/or follow-up studies. A quantitative material coefficient, which is characteristic of a particular area of the body of the patient, can be acquired, in particular with an adaptation of the detector parameter described in more detail in one of the following paragraphs. This characteristic quantitative material coefficient can be used to identify a feature pattern in a database, for example, by a statistical method or a machine learning method. The characteristic quantitative material coefficient can also be used for classification of a tissue, for example, in order to quantify the success of the irradiation of the tissue or to quantify the toxicity of the irradiation with regard to the tissue.

In principle, the use of the quantum counting X-ray detector enables an inherent spectral sensitivity of the acquired CT measurement data. In this way, as described in more detail in one or more of the following embodiments, two quantitative material coefficients can be calculated from any two-parameter model. Alternatively, or in addition, as described in more detail in one or more of the following embodiments, a quantification in relation to two linearly independent base materials is also possible. Advantageously, this leads to the possibility that, regardless of an embodiment of the CT device used and of acquisition parameters used, a set of absolute quantitative material coefficients can be used for processing in the context of the planning of the irradiation of the patient. Processing steps in the context of this processing such as, for example, the automatic contouring of the target volume and/or risk volume or with regard to monitoring a treatment, can accordingly be performed in a standardized manner.

Finally, it should be mentioned that scatter characteristics of the patient can be defined on the basis of the calculated spatially resolved distribution of the quantitative material coefficient, in particular the electron density. In this way, the spatially resolved distribution of the material coefficient can also be used as an input parameter for a scatter correction algorithm of the CT measurement data.

At least one embodiment provides that the processing of the CT measurement data comprises the calculation of a first spatially resolved distribution of a first quantitative material coefficient and a second spatially resolved distribution of a second quantitative material coefficient from the spectrally resolved CT measurement data.

Both the first spatially resolved distribution and the second spatially resolved distribution can constitute the result data in this case. The first quantitative material coefficient and the second quantitative material coefficient are in particular, differently designed and in particular, describe different physical tissue properties. Advantageously, both the first spatially resolved distribution and also the second spatially resolved distribution can be calculated on the basis of a single set of spectrally resolved measurement data.

At least one embodiment provides that the provision of the result data comprises a provision of the first spatially resolved distribution of the first quantitative material coefficient for a first dose calculation algorithm and a provision of the second spatially resolved distribution of the second quantitative material coefficient for a second dose calculation algorithm.

The first dose calculation algorithm in particular uses the first spatially resolved distribution of the first quantitative material coefficient as an input parameter for the dose calculation. In the course of the planning of the irradiation of the patient, a first dose distribution is thus calculated, in particular by the first dose calculation algorithm, taking into account the first spatially resolved distribution of the first quantitative material coefficient. Equally, the second dose calculation algorithm in particular, uses the second spatially resolved distribution of the second quantitative material coefficient as an input parameter for the dose calculation. In the course of the planning of the irradiation of the patient, a second dose distribution is thus calculated, in particular by the second dose calculation algorithm, taking into account the second spatially resolved distribution of the second quantitative material coefficient.

The first dose calculation algorithm and the second dose calculation algorithm are in particular, differently designed. Precisely by taking into account the different spatially resolved distributions of the quantitative material coefficient, the first dose calculation algorithm and the second dose calculation algorithm can thus have different dose distributions as a calculation result.

An increase in the reliability of algorithms for processing the CT measurement data is conceivable if the first quantitative material coefficient and the second quantitative material coefficient are suitably selected. According to one embodiment, the first quantitative material coefficient is an electron density and the second quantitative material coefficient is an effective atomic number. According to at least one further embodiment, the first quantitative material coefficient and the second quantitative material coefficient are based on two base materials linearly independent of each other. An example of two base materials linearly independent of each other are water and calcium. Another example is water and iodine.

At least one embodiment provides that the processing of the CT measurement data comprises a separate processing of the first spatially resolved distribution of the first quantitative material coefficient and the second spatially resolved distribution of the second quantitative material coefficient and a generation of the result data by combining the partial result data generated during the separate processing.

The first quantitative material coefficient is determined in particular, regardless of the second quantitative material coefficient. A further increase in the reliability of algorithms for processing the CT measurement data is conceivable by the separate consideration of two different quantitative material coefficients. The algorithms can, for example, be used for contouring of the target volume and/or risk volume. The algorithms can also be used for analysis of image properties in manually or semi-automatically generated contoured image volumes.

At least one embodiment provides that the acquisition of the CT measurement data comprises the loading of previously acquired spectrally resolved CT measurement data from a database for the calculation of the spatially resolved distribution of the quantitative material coefficient.

Due to the inherent energy resolution, the quantitative material coefficient can also be calculated retrospectively from spectrally resolved CT measurement data originally acquired for another purpose by the quantum counting X-ray detector. Nevertheless, the spatially resolved distribution of the quantitative material coefficient can be subsequently calculated from the spectrally resolved CT measurement data. The CT measurement data is, for example, acquired at least one day before loading from the database for calculation of the spatially resolved distribution of the quantitative material coefficient from the CT measurement data.

At least one embodiment provides that, in addition to the calculation of the spatially resolved distribution of the quantitative material coefficient from the spectrally resolved CT measurement data, the processing of the CT measurement data comprises the identification of a target volume and/or risk volume in the spectrally resolved CT measurement data.

Therefore, the spectrally resolved CT measurement data can fulfil an advantageous dual function, namely both as a basis for the calculation of the spatially resolved distribution of the quantitative material coefficient and for the identification of the target volume and/or risk volume. The acquisition of the CT measurement data can be adapted in a particularly suitable manner for the identification of the target volume and/or risk volume. This is possible in particular, to the extent that on account of the inherent spectral sensitivity of the quantum-counting X-ray detector, the acquisition of the CT measurement data need not have any particular features in order to enable the calculation of the spatially resolved distribution of the quantitative material coefficient from the spectrally resolved CT measurement data.

A further advantage of the inherent spectral sensitivity of the spectrally resolved CT measurement data acquired by the quantum counting X-ray detector is that dual-energy applications can be used as standard in the processing of the spectrally resolved CT measurement data without necessitating a special dual-energy acquisition. In this way, it is also only possible to determine that a dual-energy application is to be used in the processing of the spectrally resolved CT measurement data after the acquisition of the spectrally resolved CT measurement data. Dual energy applications enable different processing of the spectrally resolved CT measurement data and can, for example, result in improved differentiation between bone tissue and other tissues. Further possible dual-energy applications enable a particularly advantageous evaluation in specific organ regions such as, for example, in the bone marrow, in blood vessels, in the brain, etc. Dual energy applications matched to specific diseases such as gout, for example, are also conceivable.

At least one embodiment provides that the spectrally resolved CT measurement data has been acquired by such acquisition parameters of the quantum counting X-ray detector that the spectrally resolved CT measurement data displays a particularly suitable contrast between different tissue types for the identification of the target volume and/or risk volume.

The spectrally resolved CT measurement data is therefore in particular acquired in such a way that it is particularly suitable for the identification of the target volume and/or risk volume. In the acquisition of the spectrally resolved CT measurement data, the following identification of the target volume and/or risk volume in particular, is therefore paramount and not the calculation of the spatially resolved distribution of the quantitative material coefficient which is typically already possible in the acquisition of the CT measurement data due to the use of inherent spectral sensitivity of the quantum-counting X-ray detector.

In this case, the procedure is advantageous in that the spatially resolved distribution of the linear attenuation coefficient for a specific photon energy is reconstructed from the spectrally resolved CT measurement data. The specific photon energy is advantageously selected in this case, wherein the spectrally resolved CT measurement data displays a particularly suitable contrast between the different tissue types for the identification of the target volume and/or risk volume. It is also conceivable that the linear attenuation coefficient is reconstructed for different energies, in order to be able to distinguish between different types of tissue in a particularly suitable manner. In this case, a reconstruction is also conceivable in which the energy for which the linear attenuation coefficient is determined varies in a location-dependent manner. The best possible contrast-to-noise ratio can thus be obtained locally for the identification of the target volume and/or risk volume.

At least one embodiment provides that the spectrally resolved CT measurement data covers a field of view comprising both the entire body of the patient and positioning aids used for the storage of the patient in an axial measuring layer.

It is thus possible to ensure that the spatially resolved distribution of the material coefficient calculated from the spectrally resolved measurement data covers the aforementioned field of view. In this way, the quantitative material coefficient can be calculated for the sufficiently large field of view (FOV). In particular, it is important for the subsequent dose calculation using the spatially resolved distribution of the material coefficient that the part of the body of the patient and those positioning aids are positioned in the field of view for the irradiation of the patient in the therapy beam.

By using the quantum counting X-ray detector in data acquisition, the spectrally resolved CT measurement data can be calculated particularly easily for the entire field of view. In this case, the entire field of view of the CT device can serve as a field of view. In contrast to a dual-energy data acquisition, there are no further restrictions for the field of view for which the CT measurement data can be acquired with more than one energy. Furthermore, the use of the quantum counting X-ray detector for data acquisition can ensure that the spectrally resolved CT measurement data can be acquired for the entire field of view with consistent accuracy. In this way, a particularly accurate calculation of the quantitative material coefficient for the entire field of view can be achieved.

At least one embodiment provides that the processing of the CT measurement data comprises a beam hardening correction of the spectrally resolved CT measurement data using spectral information contained in the spectrally resolved CT measurement data, wherein the spatially resolved distribution of the quantitative material coefficient is calculated from the spectrally resolved CT measurement data corrected by the beam hardening correction.

Using the spectral information contained in the spectrally resolved CT measurement data, the beam hardening in the CT measurement data can be corrected particularly advantageously. Thus, the beam hardening correction of the spectrally resolved CT measurement data can comprise a decomposition of the spectrally resolved CT measurement data in water tissue and bone tissue using the spectral information contained in the spectrally resolved CT measurement data. This decomposition can advantageously replace or supplement conventional threshold value techniques used in beam hardening correction. Particularly advantageous systematic errors in the calculation of the quantitative material coefficient can be avoided by the beam hardening correction. In this way, the accuracy of a dose calculation can be advantageously increased by the spatially resolved distribution of the material coefficient calculated in this way.

At least one embodiment provides that the processing of the CT measurement data comprises the identification of a target volume and/or risk volume in the CT measurement data, wherein the provision of the result data comprises the provision of the identified target volume and/or risk volume to the interface.

In principle, the identification of the target volume and/or risk volume can be understood to mean the automatic, semi-automatic or manual segmentation and/or contouring of the target volume and/or risk volume. In this way, the result data generated by this processing presents information as to which spatial region within the CT measurement data has the identified target volume and/or risk volume. The result data can also present information as to the profile, which an outer boundary of a contour of the identified target volume and/or risk volume has within the CT measurement data. The result data can therefore present information necessary for the planning of irradiation by way of the spatial position of the target volume and/or risk volume within the CT measurement data. Of course, a plurality of target volumes and/or a plurality of risk volumes can also be identified in the spectrally resolved CT measurement data.

At least one embodiment provides that the identification of the target volume and/or risk volume comprises a differentiation of a tissue of the target volume and/or risk volume from surrounding tissue, wherein the differentiation of the tissue of the target volume and/or risk volume from surrounding tissue takes place using the specific information content of the CT measurement data resulting from the use of the at least one quantum counting X-ray detector in the acquisition of the CT measurement data.

The use of the quantum counting X-ray detector in the acquisition of the CT measurement data particularly results in each X-ray photon contributing equally to the signal in the CT measurement data. In this way, the effective X-ray spectrum detected in the CT measurement data acquired by the quantum-counting X-ray detector is typically shifted to lower energies compared with CT measurement data acquired by integrating detectors. At these lower energies, contributions of the photoelectric effect especially predominate compared to contributions of the Compton effect to the absorption of the X-ray radiation. The increased contributions of the photoelectric effect particularly result in the possibility of greater differences being measured between materials with different elemental composition in the CT measurement data. This in turn advantageously results in an increased contrast between different tissue types in the CT measurement data acquired by the quantum counting X-ray detector. Precisely the contrast between tissue types with similar electron density, but of different elemental composition, in particular with regard to elements having higher atomic numbers, can be increased by using the quantum-counting X-ray detector in the acquisition of the CT measurement data. In this way, the tissue of the target volume and/or risk volume can be particularly clearly differentiated from the surrounding tissue by the CT measurement data acquired in this way.

At least one embodiment provides that the identification of the target volume and/or risk volume comprises a differentiation of adipose tissue and muscle tissue, wherein the differentiation of the adipose tissue and muscle tissue takes place using the specific information content of the CT measurement data produced as a result of the use of the at least one quantum counting X-ray detector in the acquisition of the CT measurement data.

This procedure is particularly based on the consideration that the use of the quantum counting X-ray detector in the acquisition of the CT measurement data results in an increased contrast between adipose tissue and muscle tissue. In this way, a particularly suitable differentiation is possible between these two tissue types in the CT measurement data. In contrast, in a conventional acquisition by an integrating X-ray detector, both tissue types would appear similar in the CT measurement data as they have a similar electron density.

At least one embodiment provides that the identification of the target volume and/or risk volume comprises a differentiation of gray matter and white matter, wherein the differentiation of the gray matter and white matter takes place using the specific information content of the CT measurement data which is produced as a result of the use of the at least one quantum counting X-ray detector in the acquisition of the CT measurement data.

This procedure is particularly based on the consideration that the use of the quantum counting X-ray detector in the acquisition of the CT measurement data results in an increased contrast between gray matter and white matter. In this way, a particularly suitable differentiation between these two tissue types in the CT measurement data is possible. In contrast, in a conventional acquisition by an integrating X-ray detector, both tissue types would appear similar in the CT measurement data as they have a similar electron density.

At least one embodiment provides that the acquisition of the CT measurement data comprises the detection of spectrally resolved CT measurement data resulting from acquisition by the quantum-counting X-ray detector, the processing of the CT measurement data comprises a beam hardening correction of the spectrally resolved CT measurement data using spectral information contained in the spectrally resolved CT measurement data, and the identification of the target volume and/or risk volume comprises a differentiation of bone structures in the spectrally resolved CT measurement data corrected by the beam hardening correction.

As already described, the beam hardening correction can be carried out particularly advantageously in the spectrally resolved CT measurement data. In the spectrally resolved CT measurement data corrected by the beam hardening correction, the bone structures can be differentiated from each other particularly well. If the target volume and/or risk volume comprises a bone structure and/or a body region located directly adjacent to a bone structure, an improved identification of the target volume and/or risk volume is thus possible.

At least one embodiment provides that the bone structures are differentiated from each other in a skull base region of the patient.

Precisely the small bone structures in the skull base region can be differentiated particularly well from each other in the spectrally resolved CT measurement data corrected by the beam hardening correction.

At least one embodiment provides that the CT measurement data comprises a first CT measurement data set and a second CT measurement data set, wherein the first CT measurement data set has been acquired by a higher energy threshold of the quantum counting X-ray detector than the second CT measurement data set, the processing of the CT measurement data comprises the creation of a weighted combination of the first CT measurement data set and the second CT measurement data set, wherein combined CT measurement data is generated and the identification of the target volume and/or risk volume takes place in the combined CT measurement data.

The procedure described in this embodiment can also be referred to as photon weighting. The first CT measurement data set and the second CT measurement data set are acquired in particular by different configurations of the quantum counting X-ray detector with regard to the energy thresholds. That the first CT measurement data set has been acquired by a higher energy threshold of the quantum counting X-ray detector than the second CT measurement data set can in particular signify that on average the first CT measurement data set has been acquired at higher energy thresholds than the second CT measurement data set. The first CT measurement data set therefore advantageously has information about higher-energy photons than the second CT measurement data set. The first CT measurement data set and the second CT measurement data set in particular cover the same field of view.

The combined CT measurement data generated by photon weighting, in particular, is particularly well-suited to the identification of the target volume and/or risk volume. The information about different photon energies from the first CT measurement data set and the second CT measurement data set can be particularly advantageously combined by suitable selection of the weighting factors such that improved identification of the target volume and/or risk volume in the combined CT measurement data is possible. Weighting factors for the formation of the weighted combination can be generated in subsequent processing based on the content of the first CT measurement data set and/or second CT measurement data set. As described in more detail hereinafter, the weighting factors can be determined by rough pre-segmentation of the CT measurement data. Alternatively, or additionally, it is also conceivable that weighting factors are obtained by a machine learning method, for example, an artificial neural network, by which combined CT measurement data that is particularly suitable for the planning of the irradiation can be generated.

At least one embodiment provides that the processing of the CT measurement data comprises the extraction of information for a beam hardening correction from the first CT measurement data set, and a beam hardening correction of the combined CT measurement data based on the extracted information, wherein the identification of the target volume and/or risk volume takes place in the combined CT measurement data corrected by the beam hardening correction.

In such a way, the information from the first CT measurement data set, which is particularly characterized by higher-energy photons than the second CT measurement data set, can be used in a particularly suitable manner for the beam hardening correction.

At least one embodiment provides that the creation of the weighted combination of the first CT measurement data set and of the second CT measurement data set takes place using spatially varying weighting factors.

In this way, a weighting factor other than for a second spatial point of the CT measurement data is particularly used for the creation of the weighted combination at a first spatial point of the CT measurement data. The weighting factors can, for example, vary over different body regions of the patient.

At least one embodiment provides that the processing of the CT measurement data initially comprises a rough identification of the target volume and/or risk volume, wherein the spatially varying weighting factors are defined by the roughly segmented target volume and/or risk volume and then a fine identification of the target volume and/or risk volume takes place in the combined CT measurement data.

Thus, for example, a different weighting factor can be set for the target volume and/or risk volume than for the body regions surrounding the target volume and/or risk volume. The rough identification of the target volume and/or risk volume therefore serves advantageously to determine the weighting factors by which a particularly advantageous weighting of the first CT measurement data set and second CT measurement data set can take place such that the fine identification of the target volume and/or risk volume can take place in particularly suitably weighted combined CT measurement data.

At least one embodiment provides that the acquisition of the CT measurement data comprises the acquisition of high-resolution CT measurement data by the quantum counting X-ray detector, wherein a high-resolution mode of the quantum counting X-ray detector is used for the acquisition of the high-resolution CT measurement data, wherein in the high-resolution mode each pixel of the quantum counting X-ray detector is counted separately.

Typically, the use of the quantum counting X-ray detector intrinsically results in an increase in the resolution compared to conventional CT acquisitions as individual detector elements, also referred to as detector pixels, of the quantum counting X-ray detector must be smaller than detector elements of conventional CT detectors as separating layers between individual pixels of the quantum counting X-ray detector, which reduce the quantum efficiency at a higher pixel resolution, are unnecessary. At the same time, the problem of crosstalk between adjacent detector pixels, which typically impedes a reduction in the size of the detector pixels of conventional CT detectors, is not customarily found in the quantum counting X-ray detector.

In principle, a high resolution of the CT measurement data can thus be achieved by the use of the quantum-counting X-ray detector in all spatial directions (x, y, z) and over the entire field of view, even when using a large bore system. The resolution of the acquired CT measurement data typically depends on the number of pixels of the quantum counting X-ray detector for which the counting pulses are jointly counted. In a standard resolution mode of the quantum counting X-ray detector, typically a plurality of pixels of the quantum counting X-ray detector are jointly counted, for example, a pixel matrix of 2×2 pixels or a different type of interconnection of pixels. The proposed use of the high-resolution mode (ultra-high resolution mode, UHR mode), in which each pixel of the quantum counting X-ray detector is counted separately, can result in a particularly high resolution of the CT measurement data. This particularly high-resolution CT measurement data can then be used particularly advantageously in the planning of the irradiation of the patient.

At least one embodiment provides that the processing of the CT measurement data comprises a calculation of a spatially resolved distribution of a quantitative material coefficient from the high-resolution CT measurement data and the provision of the result data comprises a provision of the spatially resolved distribution of the quantitative material coefficient to the interface.

The high-resolution CT measurement data can be included particularly advantageously in the calculation of the quantitative material coefficient for bone tissue. The high resolution of the CT measurement data can, for example, enable improved differentiation between different bone densities of the bone tissue.

At least one embodiment provides that the high-resolution CT measurement data is included in unaltered form in the calculation of the spatially resolved distribution of the quantitative material coefficient for a bone tissue of the patient and the high-resolution CT measurement data is included in the calculation of the spatially resolved distribution of the quantitative material coefficient for a soft tissue of the patient in a reduced resolution.

This approach is based on the consideration that particularly for calculating the spatially resolved distribution of the quantitative material coefficient for the bone tissue, a higher resolution is expedient than for the soft tissue. The reason for this is that typically finer structures are distinguishable in the bone tissue than in the soft tissue. It is therefore often sufficient for the resolution of the high-resolution CT measurement data for the calculation of the spatially resolved distribution of the quantitative material coefficient for the soft tissue to be reduced. According to at least one embodiment, the reduced resolution of the high-resolution CT measurement data is generated by filtering the high-resolution CT measurement data using a filter kernel.

At least one embodiment provides that the calculation of the spatially resolved distribution of the quantitative material coefficient comprises a calculation of a spatially resolved distribution of a stopping power from the high-resolution CT measurement data and the provision of the result data comprises the provision of the spatially resolved distribution of the stopping power for the planning of particle irradiation of the patient.

Particle irradiation takes place in particular by protons, helium ions or carbon ions. As a high degree of accuracy is typically necessary for dose calculation in the case of particle irradiation, the spatially resolved distribution of the stopping power for the planning of particle irradiation can be calculated particularly advantageously by the high-resolution CT measurement data.

At least one embodiment provides that the spatially resolved distribution of the quantitative material coefficient is calculated from the high-resolution CT measurement data for at least one of the following body regions of the patient: an eye region of the patient, a body region described by the course of the trigeminal nerve of the patient, a skull base of the patient, a lung region of the patient.

The high-resolution CT measurement data can namely be used particularly advantageously for the planning of the irradiation of body regions for which a particularly high degree of accuracy is necessary. Precisely the connection with the use of a particularly precise irradiation of the aforementioned body regions, for example, a particle irradiation or a brachytherapy irradiation, is advantageously possible here. By using the high-resolution CT measurement data, namely, for example, the influence of small bone structures can be advantageously considered with the particularly precise irradiation.

At least one embodiment provides that the acquisition of the CT measurement data comprises the acquisition of spectrally resolved and temporally resolved CT measurement data resulting from acquisition by the quantum counting X-ray detector, the processing of the CT measurement data comprises the calculation of a spatially resolved and temporally resolved distribution of a quantitative material coefficient from the spectrally resolved and temporally resolved CT measurement data and the provision of the result data comprises the provision of the spatially resolved and temporally resolved distribution of the quantitative material coefficient to the interface.

Temporally resolved CT measurement data is often important for the planning of the irradiation of the patient to be able to take into account a movement of the patient, in particular a cyclic respiratory movement in planning. This can be particularly important if the target volume is in the proximity of organs, for example, the liver, which undergo particularly strong movement with the respiratory movement.

By using the quantum counting X-ray detector for acquisition of the CT measurement data, it is possible to ensure that spectrally resolved CT measurement data can also be dynamically acquired over the course of the respiratory movement of the patient. This spectrally resolved CT measurement data can have a full temporal and spatial coherence over the course of the respiratory movement of the patient. In this way, the aforementioned dual-energy application can be advantageously employed in the processing of the spectrally resolved and temporally resolved CT measurement data. For example, over the course of the respiratory movement of the patient, suitably determined tissue of the patient can be highlighted in the CT measurement data or a time-resolved dosimetry, in particular for a target volume located in the lung for a particle therapy, is conceivable. The removal of a contrast enhancement (contrast removal) or a beam hardening correction can also take place in the temporally resolved CT measurement data.

At least one embodiment provides that the spectrally resolved and temporally resolved CT measurement data is acquired from at least one of the following body regions of the patient: a liver region of the patient, a pancreas region of the patient, a thorax region of the patient.

In particular, in the case of particularly contrast-enhanced imaging of these body regions, the spectrally resolved and temporally resolved CT measurement data can provide a particularly advantageous basis for the planning of irradiation.

At least one embodiment provides that the acquisition of the CT measurement data of the patient comprises the acquisition of the CT measurement data by the CT device having the quantum counting X-ray detector, wherein during the acquisition of the CT measurement data, a detector parameter of the quantum counting X-ray detector is changed.

The fact that a detector parameter of the quantum counting X-ray detector is changed during the acquisition of the CT measurement data in particular means that at a first instant of the acquisition of the CT measurement data, the quantum counting X-ray detector is operated with a different setting of the detector parameter than at a second instant of the acquisition of the CT measurement data. The detector parameter can be changed for different sections of the acquisition of the CT measurement data. A dynamic continuous changing of the detector parameter during the acquisition of the CT measurement data is also conceivable.

Through the static or dynamic changing of the detector parameter during data acquisition, CT measurement data, which is particularly suitable for use in the planning of the irradiation of the patient can be acquired. Possible applications are described in more detail in the following paragraphs. At this point, three particularly suitable applications should be mentioned:

- The resolution of the quantum counting X-ray detector can be specifically increased for the acquisition of the CT measurement data in a body region in which the boundaries of an organ for contouring are expected.
- The detector parameter can be adjusted such that the sensitivity and/or the soft tissue contrast in a body region in which the presence of a contrast media is to be expected is increased.
- In a body region in which the presence of a bone tissue is to be expected, the detector parameter can be adjusted such that an improved decomposition of the bone materials and/or a reduction of beam hardening artefacts can be achieved.

The aforementioned detector parameter can also be adapted after the acquisition of the CT measurement data for the reconstruction of the CT measurement data. Thus, a spatial variation in the resolution and/or energy thresholds for the reconstruction of the CT measurement data is conceivable. It is also conceivable that strips of detector elements of the quantum counting X-ray detector can be set with different detector parameters. This can enable specific reconstructions for a spiral acquisition. It is also conceivable that, based on the acquisition protocol and/or a positioning of the target volume and/or risk volume for specific regions of the quantum counting X-ray detector, only fixed detector parameters are used. This fixing of the detector parameters can vary with regard to the rotation of the detector-emitter system and/or a change in acquisition along the z-position.

At least one embodiment provides that during the acquisition of CT measurement data, an energy threshold of the quantum counting X-ray detector is changed.

In particular, an energy threshold of the quantum counting X-ray detector or else a plurality of energy thresholds of the quantum counting X-ray detector can be changed during the acquisition of the CT measurement data. If a plurality of energy thresholds of the quantum counting X-ray detector are changed during the acquisition of the CT measurement data, particularly at a first instant of the acquisition of CT measurement data, the quantum counting X-ray detector is operated with a set of energy thresholds other than at a second instant of the acquisition of CT measurement data. Different photon energies can be set in keV as energy thresholds. The different energy thresholds can, for example, be set as photon energy, as voltage or as current.

By adjusting the energy threshold, the quantum counting X-ray detector can be set in such a manner that the CT measurement data is acquired in a particularly suitable manner for the planning of the irradiation, for example, locally having a particularly suitable contrast between different types of tissue for the identification of the target volume and/or risk volume.

At least one embodiment provides that during the acquisition of the CT measurement data, a resolution of the quantum counting X-ray detector is changed with regard to a combination of pixels of the quantum counting X-ray detector.

In this way, the quantum counting X-ray detector can be operated with a higher resolution at a first instant of the acquisition of the CT measurement data than at a second instant of the acquisition of the CT measurement data. At the first instant, in particular fewer pixels of the quantum counting X-ray detector are therefore jointly counted than at the second instant.

It is particularly expedient for the application to be carried out in such a way that high-resolution CT measurement data is acquired from the bone tissue of the patient, while low-resolution CT measurement data is acquired from the soft tissue of the patient. Furthermore, a higher resolution of the CT measurement data in the region of the target volume and/or risk volume than in the rest of the body of the patient is also expedient.

Furthermore, it is conceivable that a photon flux is changed during the acquisition of the CT measurement data. The quantum counting X-ray detector can particularly be adapted by adapting a bit depth of the transmission to the changed photon flux. Thus, an expected photon flux, in particular according to an adapted modulation of the X-ray tubes, can be used as an input parameter for the adaptation of the bit depth. For example, when a maximum expected count rate on the quantum-counting X-ray detector is known, the bit depth of the transmission can be correspondingly throttled. If, for example, a maximum photon flux is expected, the number of threshold values and/or detector lines and/or items of information for transmission can thus be increased by way of individual detector pixels. The photon flux can only be changed in at least one of the three spatial directions (x, y, z). The advantageous application is conceivable, for example, that in the vicinity of the target volume of the irradiation, the resolution of the quantum-counting X-ray detector is increased and at the same time a particularly high dose rate is set for acquisition from this region. In this way, there can be a sufficient dose for the size of the pixels of the quantum counting X-ray detector.

Furthermore, it is also conceivable that a linear correction parameter of the quantum counting X-ray detector is changed during the acquisition of the CT measurement data.

Different ways in which the detector parameter is changed during the acquisition of the CT measurement data are conceivable.

According to at least one embodiment, CT measurement data is respectively acquired with a possible suitable setting of the detector parameter for different body regions.

According to at least a first embodiment, the detector parameter of the quantum counting X-ray detector is changed during the acquisition of the CT measurement data such that for an acquisition of the CT measurement data at a first z-position along a longitudinal direction of the patient, a first setting of the detector parameter is set and for an acquisition of the CT measurement data at a second z-position along the longitudinal direction of the patient, a second setting of the detector parameter is set.

According to at least a second embodiment, the detector parameter of the quantum counting X-ray detector is changed during the acquisition of the CT measurement data such that for an acquisition of the CT measurement data at a first rotational position of a detector-emitter system of the CT device, a first setting of the detector parameter is set and for an acquisition of the CT measurement data at a second rotational position of the detector-emitter system of the CT device, a second setting of the detector parameter is set.

According to at least a third embodiment, the detector parameter of the quantum counting X-ray detector is changed during the acquisition of the CT measurement data such that for an acquisition of the CT measurement data of a first body region of the patient, a first setting of the detector parameter is set and for an acquisition of the CT measurement data of a second body region of the patient, a second setting of the detector parameter is set.

In the following embodiments, the possibility is described in more detail of the first setting of the detector parameter being set for the acquisition of the CT measurement data of the first body region of the patient and the second setting of the detector parameter being set for the acquisition of the CT measurement data of the second body region of the patient. The embodiments can largely also be applied to the other possibilities.

At least one embodiment provides that the first body region and the second body region are established by existing medical image data of the patient and/or using an Atlas database before the acquisition of the CT measurement data.

There may already be a contour of an organ structure for the existing medical image data of the patient. The contour of the organ structure can be used in establishing the first body region and the second body region. It is also conceivable that the contour of the organ structure is established on the basis of the information contained in the Atlas database. By this approach, a detector parameter other than for the acquisition of the remaining CT measurement data can be set for the acquisition of the CT measurement data from the organ structure. According to at least one embodiment, the first body region comprises a target volume of the irradiation and the second body region comprises a body region outside the target volume of the irradiation.

At least one embodiment provides that the first body region is embodied such that it is positioned in a beam region for the irradiation of the patient, and the second body region is embodied such that it is positioned outside a beam region for the irradiation of the patient.

The beam region is known in particular from beam settings of the radiotherapy device, which are established by an existing irradiation plan.

At least one embodiment provides that the first body region and the second body region are embodied such that for the irradiation of the patient a higher radiation dose is provided for the first body region than for the second body region.

A known three-dimensional dose distribution from an existing irradiation plan can be used in this way as input information for the establishment of the detector parameter. The detector parameter can then be established in such a way that particularly for an optimization and/or adjustment of the existing irradiation plan, suitable CT measurement data can be acquired. This procedure is based in particular on the consideration that for the first body region, for which a higher radiation dose is provided, more precise imaging is necessary than for the second body region, for which a lower radiation dose is provided. It is also conceivable that the CT measurement data must display greater precision for those body regions in which there is a steep dose gradient, for example, close to the Bragg peak for a particle therapy or close to a position of brachytherapy applicators or in the vicinity of the target volume and/or risk volume.

At least one embodiment provides that during the acquisition of the CT measurement data, the detector parameter of the quantum counting X-ray detector is changed such that for the acquisition of the CT measurement data from the first body region of the patient, a higher resolution of the quantum counting X-ray detector is set than for the acquisition of the CT measurement data from the second body region of the patient.

This advantageous procedure is based on the consideration that higher resolution CT measurement data is more expedient for the first body region than for the second body region.

Alternatively, or in addition, it is also conceivable that external camera data, for example, 3-D camera data, is used to establish the body region, for example, the neck-shoulder region, in which the detector parameter is to be adjusted for acquisition by the quantum counting X-ray detector.

At least one embodiment provides that the interface acquires further measurement data, which is acquired via an imaging device of a radiotherapy device used for the irradiation of the patient, wherein the result data is set in relation to the further measurement data for the planning of the irradiation of the patient.

By using the quantum counting X-ray detector for the acquisition of CT measurement data, the result data can be set in relation to the further measurement data with greater ease. For example, a simpler scatter correction is possible.

At least one embodiment provides that the imaging device of the radiotherapy device used for the irradiation of the patient likewise has a quantum counting X-ray detector, wherein the result data is set in relation to the further measurement data using a specific information content of the CT measurement data and the further CT measurement data resulting from the use of the quantum counting X-ray detector in the acquisition of the CT measurement data and the further measurement data.

Using the additional specific information content, the CT measurement data can be set in relation to the further measurement data with particular ease.

At least one embodiment provides that the CT measurement data comprises at least two CT measurement data sets acquired at different instants, wherein the at least two CT measurement data sets are registered using the specific information content of the CT measurement data resulting from the use of the at least one quantum counting X-ray detector in the acquisition of the CT measurement data, wherein the registered at least two CT measurement data sets are made available to the interface.

In this way, a registration of the at least two CT measurement data sets can be improved. This can be expedient for special CT applications, for example, perfusion imaging and/or functional imaging, in particular the lung of the patient.

In the following two embodiments, two more applications are described in which a contrast media-based acquisition of the CT measurement data can be suitably performed and evaluated by the quantum counting X-ray detector: at least the first embodiment provides that during the acquisition of the CT measurement data, a contrast media has been used, wherein the processing of the CT measurement data comprises a material decomposition of the CT measurement data in tissue having contrast media, and comprises other tissue using the specific information content of the CT measurement data resulting from the use of the at least one quantum counting X-ray detector in the acquisition of the CT measurement data. At least the second embodiment provides that during the acquisition of the CT measurement data a contrast media has been used, wherein the processing of the CT measurement data comprises the creation of a virtual non-contrasted CT image using the specific information content of the CT measurement data resulting from the use of the at least one quantum counting X-ray detector in the acquisition of the CT measurement data. Here, k-edge imaging can be used to create the virtual non-contrasted image.

Finally, it is also conceivable that the processing of the CT measurement data comprises the detection and/or quantification of metal nanoparticles which are located in the patient to increase the effect of the irradiation of the patient, using the specific information content of the CT measurement data resulting from the use of the at least one quantum counting X-ray detector in the acquisition of the CT measurement data.

The arithmetic unit according to at least one embodiment of the invention comprises at least one calculation module, wherein the arithmetic unit is designed to perform a method according to the at least one embodiment of the invention.

In this way, the arithmetic unit is designed to perform a method for the provision of result data, which is suitable for use in the planning of the irradiation of a patient. The calculation module is designed for the acquisition of CT measurement data of the patient which has been acquired via a CT device having a quantum counting X-ray detector, for the processing of the CT measurement data, wherein a specific information content of the CT measurement data resulting from the use of the quantum counting X-ray detector in the acquisition of the CT measurement data is taken into account for the processing of the CT measurement data, wherein for the processing of the CT measurement data, result data is generated which is suitable for use in the planning of the irradiation of the patient, and for the provision of result data to an interface such that the result data can be used for the planning of the irradiation of the patient.

For the most part, the components of the arithmetic unit can be embodied in the form of software components. In principle, however, these components can also be partly realized, in particular in the case of particularly rapid calculations, in the form of software-supported hardware components, for example, FPGAs or the like. Likewise, the required interfaces can be designed as software interfaces, for example, if all that is involved is a transfer of data from other software components. However, they can also be designed as hardware interfaces, which are controlled by suitable software. Of course, it is also conceivable that a plurality of the aforementioned components is realized in a combined manner in the form of an individual software component and/or software-supported hardware component.

The CT device according to at least one embodiment of the invention comprises the arithmetic unit according to at least one embodiment of the invention.

The arithmetic unit can be designed to transmit control signals to the CT device and/or to receive and/or process control signals in order to perform a method according to at least one embodiment of the invention. The arithmetic unit can be incorporated into the CT device. The arithmetic unit can also be installed separately from the CT device. The arithmetic unit can be connected to the CT device.

The computer program product according to at least one embodiment of the invention can be loaded directly into the memory of a programmable arithmetic unit and has program code to perform a method according to at least one embodiment of the invention if the computer program product is performed in the arithmetic unit. The computer program product can be a computer program or comprise a computer program. As a result, the method according to at least one embodiment of the invention can be performed quickly, repeated identically and robustly. The computer program product is configured such that it can perform the steps according to at least one embodiment of the invention via the arithmetic unit. The arithmetic unit must in each case meet the requirements such as, for example, a corresponding working memory, a corresponding graphics card or a corresponding logic unit such that the respective steps can be carried out efficiently. The computer program product is stored, for example, on a machine-readable medium or on a network or server from where it can be loaded into the processor of a local arithmetic unit. Furthermore, control information of the computer program product can be stored on an electronically readable data carrier. The control information of the electronically readable data carrier can be designed such that it performs a method according to at least one embodiment of the invention when the data carrier is used in an arithmetic unit. The computer program product can thus also represent the electronically readable data carrier. Examples of electronically readable data carriers are a DVD, a magnetic tape, a hard disk or a USB stick on which electronically readable control information, in particular software (cf. above), is stored. If this control information (software) is read by the data carrier and stored in a control system and/or arithmetic unit, one or more embodiments according to the invention of the previously described method can be performed. One or more embodiments of the invention can thus also originate from the aforementioned machine-readable medium and/or the aforementioned electronically readable data carrier.

The advantages of the arithmetic unit according to at least one embodiment of the invention, of the CT device according to at least one embodiment of the invention and of the computer program product according to at least one embodiment of the invention essentially correspond to the advantages of the method according to at least one embodiment of the invention described in detail previously. Features, advantages or alternative embodiments mentioned here are likewise also applicable to the other embodiments and vice versa. In other words, the subject claims can also be developed with the features, which are described or claimed in connection with a method. The corresponding functional features of the method are embodied by corresponding subject modules, in particular by hardware modules.

BRIEF DESCRIPTION OF THE DRAWINGS

Hereinafter the embodiments of the invention is described and explained in more detail with reference to the exemplary embodiments illustrated in the figures.

The figures show.

DETAILED DESCRIPTION

Figure 1:
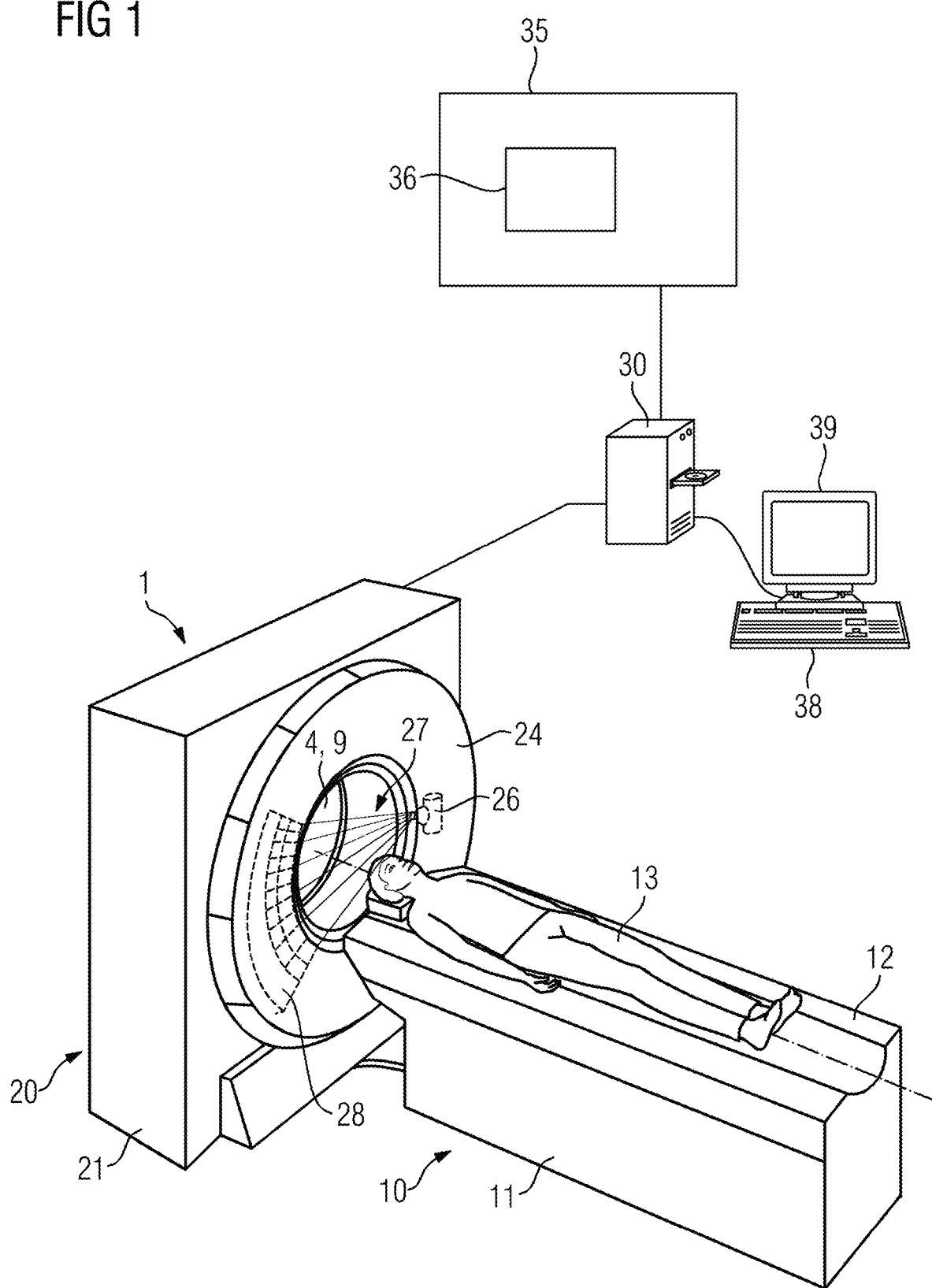
FIG. 1: A CT device according to the embodiments of the invention with an arithmetic unit according to at least one embodiment of the invention.

A quantum counting X-ray detector, also referred to as a direct-converting X-ray detector or photon-counting X-ray detector, enables the direct conversion of a high-energy photon into electron-hole pairs when the high-energy photon impinges on a semiconductor material of the quantum counting X-ray detector. The electrons generated in the semiconductor material can subsequently be converted into an electrical signal pulse in an integrated circuit. A pulse height of the signal pulse can correlate with the energy of the high-energy photon. By establishing suitable energy thresholds, individual detected high-energy photons can thus be counted in different energy bands.

In the field of computer tomography, the use of quantum counting X-ray detector enables various advantages. Thus, the CT measurement data acquired by the CT device can have an intrinsic spectral sensitivity as the energy of the detected photons, as explained in the previous section, can be directly detected. Furthermore, the CT measurement data acquired by the CT device has an intrinsic high resolution as the detector elements of the quantum counting X-ray detector are typically smaller than the detector elements of conventional X-ray detectors. Furthermore, quantum counting X-ray detector customarily perform well at low signal intensity as typically electronic noise is almost completely suppressed as the electronic noise is below the first energy threshold set. Furthermore, the counting of individual photons enables the reduction of an inherent energy weighting of the quantum counting X-ray detector.

At least one embodiment is directed to a method for the provision of result data, which is particularly suitable for use in a planning of an irradiation of a patient.

The method, according to at least one embodiment, for the provision of result data which is suitable for use in a planning of an irradiation of a patient comprises:

The acquisition of CT measurement data of the patient, which has been acquired by a CT device having a quantum counting X-ray detector, The processing of the CT measurement data, wherein the specific information content of the CT measurement data resulting from the use of the quantum counting X-ray detector in the acquisition of the CT measurement data is considered when processing the CT measurement data, wherein result data which is suitable for use in the planning of irradiation of the patient is generated when processing the CT measurement data, The provision of the result data to an interface such that the result data can be used for the planning of irradiation of the patient.

In general, the use of a quantum counting X-ray detector can enable the acquisition of CT measurement data, which is particularly suitable for use in the planning of the irradiation of the patient. Furthermore, by suitable processing of the acquired CT measurement data, which is particularly advantageously matched to the specific information content of the CT measurement data, result data can be generated which is particularly suitable for use in the planning of the irradiation of the patient.

Various requirements can be imposed on CT measurement data and/or on result data processed from the CT measurement data so that this data is particularly suitable for use in the planning of the irradiation of the patient:

It can be advantageous that the CT measurement data has a high resolution and/or a high soft tissue contrast (with or without contrast media) so that a target volume and/or risk volume can be identified and differentiated for irradiation as precisely as possible in the processing of the CT measurement data. Furthermore, this requirement can also be decisive where movement of the organs of the patient occurs, for example, in the region of the thorax, abdomen or pelvis. The CT measurement data should in particular be suitable for the identification of organ boundaries of the organs which, for example, takes place via manual, semi-automatic or automatic contouring and/or segmentation. Thus, for example, a differentiation between muscle tissue and adipose tissue or between gray and white matter may be necessary when processing the CT measurement data. Furthermore, functional CT measurement data such as, for example, perfusion measurement data or ventilation measurement data, can be used advantageously for contouring the target volume and/or risk volume.

For dose calculation in the planning of irradiation, particularly in particle therapy with protons or carbon ions, it is particularly important that, in the processing of the CT measurement data, quantitative material coefficients such as, for example, an electron density and/or a mass density and/or an effective atomic number and/or a stopping power can be reliably derived from the CT measurement data. The quantitative material coefficients can then serve as a basis for a dose calculation for the planning of the irradiation of the patient. In particular, in the case of particle therapy, the irradiation of the patient with ionized particles, it is advantageous that the stopping power and/or the corresponding water equivalent path length (WEPL) is calculated on the basis of the CT measurement data. The use of the quantum counting X-ray detector also enables the acquisition of a normalizing image for each CT measurement data acquisition such that a calculation of the quantitative material coefficient can be performed in a normalized manner for contouring or dose calculation.

In the preparation of irradiation or during irradiation, CT measurement data, in particular, cone beam CT measurement data, which is acquired via a quantum counting flat-panel detector, can be used particularly advantageously for tracking of the target volume and/or the risk volume. The CT measurement data acquired via the quantum counting X-ray detector can then be used particularly advantageously to verify the positioning of the patient, in particular, the target volume, for irradiation. Likewise, the performance of online dosimetry is conceivable.

Finally, CT measurement data can be used particularly advantageously for monitoring a course of treatment, for example, for follow-up examinations. Thus, a reaction of the tissue to the irradiation, for example, in the form of an inflammation, a tumor regression or tumor progression, can be monitored via the CT measurement data. Accordingly, irradiation parameters for the irradiation of the patient can subsequently be suitably adapted within the meaning of adaptive irradiation. A response by the patient to the irradiation can also be examined by an evaluation of tumor parameters such as, for example, tumor size and/or tumor volume and/or angiogenesis, and by comparing these tumor parameters with previous measurements. The CT measurement data acquired via the quantum counting X-ray detector, together with the recognition of specific image features, for example, texture parameters, can be used in a particularly suitable manner in the target volume and/or risk volume to support or enable the taking of treatment decisions for the patient.

Hereinafter a description is to be provided of how CT measurement data can be acquired via the use of the quantum counting X-ray detector, which can at least partially meet the aforementioned requirements in a particularly suitable manner. A particularly suitable processing of the CT measurement data for use in the planning of the irradiation of the patient is also to be examined.

The CT device can be a typical CT device, which is used for the acquisition of planning image data for the planning of irradiation of the patient. In this case, the CT measurement data is customarily acquired before the start of the initial irradiation of the patient. The irradiation of the patient then customarily takes place at least one day after the acquisition of the CT measurement data. Furthermore, in this case the CT device is typically positioned in an examination room, which is spatially separated from a treatment room in which the irradiation of the patient takes place via the radiotherapy device.

However, it is also conceivable that the CT device is installed in the treatment room, in particular a radiation booth, in which the irradiation of the patient takes place via the radiotherapy device, together with the radiotherapy device. The CT device can then constitute part of the radiotherapy device or be installed separately from the radiotherapy device. The patient support device can go backwards and forwards between the radiotherapy device and the CT device. In the case described in this paragraph, the acquired CT measurement data can be used particularly advantageously for the adaptive planning of the irradiation of the patient, in particular for an adaptation of an already existing irradiation plan, and/or for a verification of a positioning of the patient for irradiation.

In special cases, it is also conceivable that the CT device has a C-arm, wherein the X-ray source and the at least one quantum counting X-ray detector are attached at opposite ends of the C-arm.

CT measurement data is in particular projection data acquired via the CT device or image data reconstructed from the projection data. The acquisition of the CT measurement data may comprise loading the CT measurement data acquired via the quantum counting X-ray detector from a database. The acquisition of the CT measurement data may also comprise the acquisition of the CT measurement data via the quantum counting X-ray detector.

The CT measurement data, which has been acquired via the quantum counting X-ray detector, may also be cone beam CT measurement data (CBCT measurement data). The CBCT measurement data is acquired in particular when the patient is already positioned on a patient support device of the radiotherapy device for irradiation by the radiotherapy device. The CBCT measurement data is acquired in particular when the patient is positioned in such a way that he need no longer be rearranged for irradiation by the radiotherapy device. The CBCT measurement data is acquired in particular immediately before the start of the irradiation of the patient or when the irradiation of the patient has already started. In this case, in particular an imaging device of the radiotherapy device has the quantum counting X-ray detector. In this case, the CBCT measurement data acquired in this way can be acquired for different advantageous applications within the framework of the planning and/or preparation of the irradiation of the patient:

For adaptive planning of the irradiation of the patient, in particular for adapting an existing irradiation plan,
For online dosimetry,
For verification of a positioning of the patient for irradiation,
For monitoring of the target volume and/or risk volume during the performance of the irradiation of the patient, in particular during a respiratory motion of the patient.

The CBCT measurement data can be used for one or any combination of the aforementioned applications.

In the event of the use of the CBCT measurement data acquired via the quantum counting X-ray detector for online dosimetry, an increase in the accuracy of the radiation dose supplied to the patient is conceivable. In particular, a direct calculation of the radiation dose from the CBCT measurement data is conceivable. In this way, it is possible to dispense with model-based methods for dose calculation. The quantum counting X-ray detector can advantageously detect small differences in the level of the radiation dose, which is supplied to different organs of the patient, for example, the lungs or bones.

The processing of the CT measurement data takes place in particular by a processing algorithm, wherein the CT measurement data is included as input parameters in the processing algorithm. The output parameters of the processing algorithm are generated, in particular, the result data. The processing of the CT measurement data comprises in particular at least one such processing step that is generated from the CT measurement data result data, which is suitable for use in the planning of the irradiation of the patient. In this way, the processing of the CT measurement data can comprise the conversion of the CT measurement data, for example, into a spatially resolved distribution of a material coefficient. The processing of the CT measurement data can also comprise the contouring and/or segmentation of an organ structure, in particular of the target volume and/or risk volume in the CT measurement data. Of course, further possibilities for processing the CT measurement data are conceivable. Various possibilities for processing the CT measurement data are described in the description of the embodiments.

The specific information content of the CT measurement data results from the use of the quantum counting X-ray detector for the acquisition of the CT measurement data. Thus, the specific information content of the CT measurement data can, for example, be a spectral resolution of the CT measurement data resulting from the inherent energy sensitivity of the quantum counting X-ray detector. It is also conceivable that the specific information content is a particularly high spatial resolution of the CT measurement data resulting from the use of the quantum counting X-ray detector for the acquisition of the CT measurement data. In principle, the use of the quantum counting X-ray detector can also simplify the processing of the CT measurement data such that suitable result data is generated particularly easily from the CT measurement data. Then the specific information content of the CT measurement data lies in the particular suitability of the CT measurement data for processing into result data, which is suitable for use in the planning of the irradiation of the patient. The specific information content of the CT measurement data can also result from the especially skillful acquisition of the CT measurement data, which is only possible as a result of the use of the quantum counting X-ray detector.

The specific information content of the CT measurement data is in particular taken into consideration in the processing of the CT measurement data such that particularly simple and/or efficient processing of the CT measurement data for generation of the result data is enabled. The specific information content of the CT measurement data can also enable the suitable processing of the CT measurement data in the first place.

Result data, which is particularly suitable for use in the planning of the irradiation of the patient, can thus be generated by the processing of the CT measurement data. The result data can take various forms, for example, it can be available in the form of a spatially resolved distribution of a material coefficient or a contour of an organ structure. In principle, the result data constitutes suitable input parameters for an irradiation planning algorithm by which an irradiation plan can be drawn up for the irradiation of the patient. Of course, besides the result data, other data can be included as input parameters in the irradiation planning algorithm. The CT measurement data acquired by the quantum counting X-ray detector can, for example, together with measurement data from other imaging modalities, for example, MR measurement data or PET measurement data, be included in the planning of the irradiation of the patient.

The irradiation planning algorithm can, in particular, access the interface, in particular the result data provided to the interface, to perform the actual planning of the irradiation of the patient. The planning of the irradiation of the patient is thus, as described in the following embodiment, a particularly advantageous, in particular downstream step of the method according to at least one embodiment of the invention.

At least one embodiment provides that the method comprises the following additional step: the performance of the planning of the irradiation of the patient, wherein the result data is retrieved from the interface and is used for the planning of the irradiation of the patient.

In this case, the irradiation planning algorithm in particular accesses the result data stored in the interface in order to retrieve and use this in the planning of the irradiation of the patient. For example, the result data may constitute the spatially resolved distribution of a material coefficient, which can be used as input parameters for a dose calculation irradiation planning algorithm. According to a further possibility, the result data comprises the contouring of a target volume and/or risk volume, which can be used as the basis for the planning of the irradiation. The result data can, of course, also be included in the planning of the irradiation in a way which otherwise appears expedient to a person skilled in the art.

At least one embodiment provides that the acquisition of the CT measurement data comprises the acquisition of spectrally resolved CT measurement data resulting from acquisition by the quantum counting X-ray detector, the processing of the CT measurement data comprises a calculation of a spatially resolved distribution of a quantitative material coefficient from the spectrally resolved CT measurement data and the provision of the result data comprises the provision of the spatially resolved distribution of the quantitative material coefficient to the interface.

The quantitative material coefficient in particular characterizes a physical property of the tissue. Accordingly, the quantitative material coefficient customarily has a physical unit. The quantitative material coefficient is calculated in particular for each voxel of the CT measurement data. The quantitative material coefficient can be selected from the following list: an electron density, a mass density, an effective atomic number, a linear attenuation coefficient for a certain energy or for a spectrum comprising a plurality of energies, a stopping power, a water equivalent path length (WEPL), a quantitative elemental composition of the tissue. Of course, a plurality of quantitative material coefficients constituting an arbitrary selection from this list can also be calculated. In addition, of course, further quantitative material coefficients, which appear expedient to a person skilled in the art, are conceivable.

The spatially resolved distribution of the quantitative material coefficient can be calculated particularly suitably from the CT measurement data acquired by the quantum counting X-ray detector. A reason for this is, in particular, that the CT measurement data can be spectrally resolved due to acquisition by the quantum counting X-ray detector. This means, in particular, that for the acquisition of the CT measurement data from the quantum counting X-ray detector and the X-ray tubes of the CT device, there is a suitable configuration for acquiring CT measurement data for at least two different energy spectra. Due to the inherent energy resolution, the quantitative material coefficient can also be calculated retrospectively from spectrally resolved CT measurement data originally acquired for another purpose by the quantum counting X-ray detector. This procedure is described in more detail in one or more of the following embodiments.

The use of spectrally resolved CT measurement data for the calculation of the quantitative material coefficient is advantageously compared with the use of conventional CT measurement data, which is only available for an individual energy and/or an individual energy spectrum. The quantitative material coefficient can namely be calculated in particular directly from the spectrally resolved CT measurement data. In particular, only the spectrally resolved CT measurement data can then be included in the calculation of the spatially resolved distribution of the quantitative material coefficient.

In contrast, the quantitative material coefficient can typically only be calculated indirectly from the conventional CT measurement data. For typically the Hounsfield values (HU values) of the conventional CT measurement data cannot be used directly for the calculation of the quantitative material coefficient as they do not comprise any spectrally resolved energy information, but the attenuation in a given material is customarily a function of the energy. In order to enable the quantitative material coefficient to be calculated from conventional CT measurement data, typically a calibration measurement and storage of a conversion rule in a look-up table is therefore necessary. It follows from this that for conventional CT acquisition, limitations must customarily be implemented, for example, the tube voltage may not be altered.

These disadvantages can be addressed in a particularly suitable manner through the use of the quantum counting X-ray detector for the acquisition of the spectrally resolved CT measurement data because due to the energy resolution, the spectrally resolved CT measurement data can advantageously be directly included in the calculation of the quantitative material coefficient. Thus, the calibration measurement, which is customarily necessary for the conventional CT measurement data, can be advantageously omitted. Furthermore, limitations in the acquisition of the spectrally resolved CT measurement data can be advantageously omitted.

In addition, the quality and/or accuracy of the quantitative material coefficient reconstructed from the spectrally resolved CT measurement data is advantageously higher than from conventional CT measurement data. Reasons for this are, for example, that dependence on the calibration measurement and thus on the acquisition parameters selected in the acquisition can be omitted. In addition, dependence on an elemental composition of the tissue, which possibly influences the conversion rule ascertained in calibration, can be omitted.

Furthermore, the spectrally resolved CT measurement data can be acquired in an optimized manner for additional tasks by the quantum counting X-ray detector, for example, particularly optimized for subsequent contouring of the target volume and/or risk volume. For example, a particularly suitable contrast-to-noise ratio (CNR) can be ensured in the spectrally resolved CT measurement data such that, in addition to the calculation of the quantitative material coefficient, the spectrally resolved CT measurement data is also particularly suitable for contouring. It is advantageously unnecessary to establish which quantitative material coefficient should be reconstructed from the spectrally resolved CT measurement data in the run-up to acquisition of the spectrally resolved CT measurement data. Ideally, it is unnecessary to adapt acquisition parameters to the acquisition of spectrally resolved CT measurement data so that the quantitative material coefficient can be reconstructed from the spectrally resolved CT measurement data. Furthermore, it is conceivable that different quantitative material coefficients are reconstructed from the spectrally resolved CT measurement data.

The spatially resolved distribution of the quantitative material coefficient is in particular provided for a dose calculation algorithm. Of course, other applications of the quantitative material coefficient are also conceivable with regard to the planning of the irradiation of the patient.

A standardized acquisition protocol is advantageously defined for the acquisition of the spectrally resolved CT measurement data. The quantitative material coefficient can thus be advantageously reconstructed in a standardized manner directly from the spectrally resolved CT measurement data. The standardized acquisition protocol comprises, for example, standardized energy thresholds, which are particularly suitable for the calculation of the quantitative material coefficient, for example, the electron density. Furthermore, the standardized acquisition of the spectrally resolved CT measurement data can facilitate the processing of the spatially resolved distribution of a quantitative material coefficient from the spectrally resolved CT measurement data. For example, a standardized calculation of spatially resolved distributions of two different quantitative material coefficients from the spectrally resolved CT measurement data is particularly advantageous. These two-parameter models can provide a particularly suitable basis for the planning of the irradiation of the patient. This procedure is described in more detail in one or more of the following embodiments.

The quantitative material coefficient calculated by the CT measurement data can also be used in a suitable manner for radiomics studies and/or follow-up studies. A quantitative material coefficient, which is characteristic of a particular area of the body of the patient, can be acquired, in particular with an adaptation of the detector parameter described in more detail in one of the following paragraphs. This characteristic quantitative material coefficient can be used to identify a feature pattern in a database, for example, by a statistical method or a machine learning method. The characteristic quantitative material coefficient can also be used for classification of a tissue, for example, in order to quantify the success of the irradiation of the tissue or to quantify the toxicity of the irradiation with regard to the tissue.

In principle, the use of the quantum counting X-ray detector enables an inherent spectral sensitivity of the acquired CT measurement data. In this way, as described in more detail in one or more of the following embodiments, two quantitative material coefficients can be calculated from any two-parameter model. Alternatively, or in addition, as described in more detail in one or more of the following embodiments, a quantification in relation to two linearly independent base materials is also possible. Advantageously, this leads to the possibility that, regardless of an embodiment of the CT device used and of acquisition parameters used, a set of absolute quantitative material coefficients can be used for processing in the context of the planning of the irradiation of the patient. Processing steps in the context of this processing such as, for example, the automatic contouring of the target volume and/or risk volume or with regard to monitoring a treatment, can accordingly be performed in a standardized manner.

Finally, it should be mentioned that scatter characteristics of the patient can be defined on the basis of the calculated spatially resolved distribution of the quantitative material coefficient, in particular the electron density. In this way, the spatially resolved distribution of the material coefficient can also be used as an input parameter for a scatter correction algorithm of the CT measurement data.

At least one embodiment provides that the processing of the CT measurement data comprises the calculation of a first spatially resolved distribution of a first quantitative material coefficient and a second spatially resolved distribution of a second quantitative material coefficient from the spectrally resolved CT measurement data.

Both the first spatially resolved distribution and the second spatially resolved distribution can constitute the result data in this case. The first quantitative material coefficient and the second quantitative material coefficient are in particular, differently designed and in particular, describe different physical tissue properties. Advantageously, both the first spatially resolved distribution and also the second spatially resolved distribution can be calculated on the basis of a single set of spectrally resolved measurement data.

At least one embodiment provides that the provision of the result data comprises a provision of the first spatially resolved distribution of the first quantitative material coefficient for a first dose calculation algorithm and a provision of the second spatially resolved distribution of the second quantitative material coefficient for a second dose calculation algorithm.

The first dose calculation algorithm in particular uses the first spatially resolved distribution of the first quantitative material coefficient as an input parameter for the dose calculation. In the course of the planning of the irradiation of the patient, a first dose distribution is thus calculated, in particular by the first dose calculation algorithm, taking into account the first spatially resolved distribution of the first quantitative material coefficient. Equally, the second dose calculation algorithm in particular, uses the second spatially resolved distribution of the second quantitative material coefficient as an input parameter for the dose calculation. In the course of the planning of the irradiation of the patient, a second dose distribution is thus calculated, in particular by the second dose calculation algorithm, taking into account the second spatially resolved distribution of the second quantitative material coefficient.

The first dose calculation algorithm and the second dose calculation algorithm are in particular, differently designed. Precisely by taking into account the different spatially resolved distributions of the quantitative material coefficient, the first dose calculation algorithm and the second dose calculation algorithm can thus have different dose distributions as a calculation result.

An increase in the reliability of algorithms for processing the CT measurement data is conceivable if the first quantitative material coefficient and the second quantitative material coefficient are suitably selected. According to one embodiment, the first quantitative material coefficient is an electron density and the second quantitative material coefficient is an effective atomic number. According to at least one further embodiment, the first quantitative material coefficient and the second quantitative material coefficient are based on two base materials linearly independent of each other. An example of two base materials linearly independent of each other are water and calcium. Another example is water and iodine.

At least one embodiment provides that the processing of the CT measurement data comprises a separate processing of the first spatially resolved distribution of the first quantitative material coefficient and the second spatially resolved distribution of the second quantitative material coefficient and a generation of the result data by combining the partial result data generated during the separate processing.

The first quantitative material coefficient is determined in particular, regardless of the second quantitative material coefficient. A further increase in the reliability of algorithms for processing the CT measurement data is conceivable by the separate consideration of two different quantitative material coefficients. The algorithms can, for example, be used for contouring of the target volume and/or risk volume. The algorithms can also be used for analysis of image properties in manually or semi-automatically generated contoured image volumes.

At least one embodiment provides that the acquisition of the CT measurement data comprises the loading of previously acquired spectrally resolved CT measurement data from a database for the calculation of the spatially resolved distribution of the quantitative material coefficient.

Due to the inherent energy resolution, the quantitative material coefficient can also be calculated retrospectively from spectrally resolved CT measurement data originally acquired for another purpose by the quantum counting X-ray detector. Nevertheless, the spatially resolved distribution of the quantitative material coefficient can be subsequently calculated from the spectrally resolved CT measurement data. The CT measurement data is, for example, acquired at least one day before loading from the database for calculation of the spatially resolved distribution of the quantitative material coefficient from the CT measurement data.

At least one embodiment provides that, in addition to the calculation of the spatially resolved distribution of the quantitative material coefficient from the spectrally resolved CT measurement data, the processing of the CT measurement data comprises the identification of a target volume and/or risk volume in the spectrally resolved CT measurement data.

Therefore, the spectrally resolved CT measurement data can fulfil an advantageous dual function, namely both as a basis for the calculation of the spatially resolved distribution of the quantitative material coefficient and for the identification of the target volume and/or risk volume. The acquisition of the CT measurement data can be adapted in a particularly suitable manner for the identification of the target volume and/or risk volume. This is possible in particular, to the extent that on account of the inherent spectral sensitivity of the quantum-counting X-ray detector, the acquisition of the CT measurement data need not have any particular features in order to enable the calculation of the spatially resolved distribution of the quantitative material coefficient from the spectrally resolved CT measurement data.

A further advantage of the inherent spectral sensitivity of the spectrally resolved CT measurement data acquired by the quantum counting X-ray detector is that dual-energy applications can be used as standard in the processing of the spectrally resolved CT measurement data without necessitating a special dual-energy acquisition. In this way, it is also only possible to determine that a dual-energy application is to be used in the processing of the spectrally resolved CT measurement data after the acquisition of the spectrally resolved CT measurement data. Dual energy applications enable different processing of the spectrally resolved CT measurement data and can, for example, result in improved differentiation between bone tissue and other tissues. Further possible dual-energy applications enable a particularly advantageous evaluation in specific organ regions such as, for example, in the bone marrow, in blood vessels, in the brain, etc. Dual energy applications matched to specific diseases such as gout, for example, are also conceivable.

At least one embodiment provides that the spectrally resolved CT measurement data has been acquired by such acquisition parameters of the quantum counting X-ray detector that the spectrally resolved CT measurement data displays a particularly suitable contrast between different tissue types for the identification of the target volume and/or risk volume.

The spectrally resolved CT measurement data is therefore in particular acquired in such a way that it is particularly suitable for the identification of the target volume and/or risk volume. In the acquisition of the spectrally resolved CT measurement data, the following identification of the target volume and/or risk volume in particular, is therefore paramount and not the calculation of the spatially resolved distribution of the quantitative material coefficient which is typically already possible in the acquisition of the CT measurement data due to the use of inherent spectral sensitivity of the quantum-counting X-ray detector.

In this case, the procedure is advantageous in that the spatially resolved distribution of the linear attenuation coefficient for a specific photon energy is reconstructed from the spectrally resolved CT measurement data. The specific photon energy is advantageously selected in this case, wherein the spectrally resolved CT measurement data displays a particularly suitable contrast between the different tissue types for the identification of the target volume and/or risk volume. It is also conceivable that the linear attenuation coefficient is reconstructed for different energies, in order to be able to distinguish between different types of tissue in a particularly suitable manner. In this case, a reconstruction is also conceivable in which the energy for which the linear attenuation coefficient is determined varies in a location-dependent manner. The best possible contrast-to-noise ratio can thus be obtained locally for the identification of the target volume and/or risk volume.

At least one embodiment provides that the spectrally resolved CT measurement data covers a field of view comprising both the entire body of the patient and positioning aids used for the storage of the patient in an axial measuring layer.

It is thus possible to ensure that the spatially resolved distribution of the material coefficient calculated from the spectrally resolved measurement data covers the aforementioned field of view. In this way, the quantitative material coefficient can be calculated for the sufficiently large field of view (FOV). In particular, it is important for the subsequent dose calculation using the spatially resolved distribution of the material coefficient that the part of the body of the patient and those positioning aids are positioned in the field of view for the irradiation of the patient in the therapy beam.

By using the quantum counting X-ray detector in data acquisition, the spectrally resolved CT measurement data can be calculated particularly easily for the entire field of view. In this case, the entire field of view of the CT device can serve as a field of view. In contrast to a dual-energy data acquisition, there are no further restrictions for the field of view for which the CT measurement data can be acquired with more than one energy. Furthermore, the use of the quantum counting X-ray detector for data acquisition can ensure that the spectrally resolved CT measurement data can be acquired for the entire field of view with consistent accuracy. In this way, a particularly accurate calculation of the quantitative material coefficient for the entire field of view can be achieved.

At least one embodiment provides that the processing of the CT measurement data comprises a beam hardening correction of the spectrally resolved CT measurement data using spectral information contained in the spectrally resolved CT measurement data, wherein the spatially resolved distribution of the quantitative material coefficient is calculated from the spectrally resolved CT measurement data corrected by the beam hardening correction.

Using the spectral information contained in the spectrally resolved CT measurement data, the beam hardening in the CT measurement data can be corrected particularly advantageously. Thus, the beam hardening correction of the spectrally resolved CT measurement data can comprise a decomposition of the spectrally resolved CT measurement data in water tissue and bone tissue using the spectral information contained in the spectrally resolved CT measurement data. This decomposition can advantageously replace or supplement conventional threshold value techniques used in beam hardening correction. Particularly advantageous systematic errors in the calculation of the quantitative material coefficient can be avoided by the beam hardening correction. In this way, the accuracy of a dose calculation can be advantageously increased by the spatially resolved distribution of the material coefficient calculated in this way.

At least one embodiment provides that the processing of the CT measurement data comprises the identification of a target volume and/or risk volume in the CT measurement data, wherein the provision of the result data comprises the provision of the identified target volume and/or risk volume to the interface.

In principle, the identification of the target volume and/or risk volume can be understood to mean the automatic, semi-automatic or manual segmentation and/or contouring of the target volume and/or risk volume. In this way, the result data generated by this processing presents information as to which spatial region within the CT measurement data has the identified target volume and/or risk volume. The result data can also present information as to the profile, which an outer boundary of a contour of the identified target volume and/or risk volume has within the CT measurement data. The result data can therefore present information necessary for the planning of irradiation by way of the spatial position of the target volume and/or risk volume within the CT measurement data. Of course, a plurality of target volumes and/or a plurality of risk volumes can also be identified in the spectrally resolved CT measurement data.

At least one embodiment provides that the identification of the target volume and/or risk volume comprises a differentiation of a tissue of the target volume and/or risk volume from surrounding tissue, wherein the differentiation of the tissue of the target volume and/or risk volume from the surrounding tissue takes place using the specific information content of the CT measurement data resulting from the use of the at least one quantum counting X-ray detector in the acquisition of the CT measurement data.

The use of the quantum counting X-ray detector in the acquisition of the CT measurement data particularly results in each X-ray photon contributing equally to the signal in the CT measurement data. In this way, the effective X-ray spectrum detected in the CT measurement data acquired by the quantum-counting X-ray detector is typically shifted to lower energies compared with CT measurement data acquired by integrating detectors. At these lower energies, contributions of the photoelectric effect especially predominate compared to contributions of the Compton effect to the absorption of the X-ray radiation. The increased contributions of the photoelectric effect particularly result in the possibility of greater differences being measured between materials with different elemental composition in the CT measurement data. This in turn advantageously results in an increased contrast between different tissue types in the CT measurement data acquired by the quantum counting X-ray detector. Precisely the contrast between tissue types with similar electron density, but of different elemental composition, in particular with regard to elements having higher atomic numbers, can be increased by using the quantum-counting X-ray detector in the acquisition of the CT measurement data. In this way, the tissue of the target volume and/or risk volume can be particularly clearly differentiated from the surrounding tissue by the CT measurement data acquired in this way.

At least one embodiment provides that the identification of the target volume and/or risk volume comprises a differentiation of adipose tissue and muscle tissue, wherein the differentiation of the adipose tissue and muscle tissue takes place using the specific information content of the CT measurement data produced as a result of the use of the at least one quantum counting X-ray detector in the acquisition of the CT measurement data.

This procedure is particularly based on the consideration that the use of the quantum counting X-ray detector in the acquisition of the CT measurement data results in an increased contrast between adipose tissue and muscle tissue. In this way, a particularly suitable differentiation is possible between these two tissue types in the CT measurement data. In contrast, in a conventional acquisition by an integrating X-ray detector, both tissue types would appear similar in the CT measurement data as they have a similar electron density.

At least one embodiment provides that the identification of the target volume and/or risk volume comprises a differentiation of gray matter and white matter, wherein the differentiation of the gray matter and white matter takes place using the specific information content of the CT measurement data which is produced as a result of the use of the at least one quantum counting X-ray detector in the acquisition of the CT measurement data.

This procedure is particularly based on the consideration that the use of the quantum counting X-ray detector in the acquisition of the CT measurement data results in an increased contrast between gray matter and white matter. In this way, a particularly suitable differentiation between these two tissue types in the CT measurement data is possible. In contrast, in a conventional acquisition by an integrating X-ray detector, both tissue types would appear similar in the CT measurement data as they have a similar electron density.

At least one embodiment provides that the acquisition of the CT measurement data comprises the detection of spectrally resolved CT measurement data resulting from acquisition by the quantum-counting X-ray detector, the processing of the CT measurement data comprises a beam hardening correction of the spectrally resolved CT measurement data using spectral information contained in the spectrally resolved CT measurement data, and the identification of the target volume and/or risk volume comprises a differentiation of bone structures in the spectrally resolved CT measurement data corrected by the beam hardening correction.

As already described, the beam hardening correction can be carried out particularly advantageously in the spectrally resolved CT measurement data. In the spectrally resolved CT measurement data corrected by the beam hardening correction, the bone structures can be differentiated from each other particularly well. If the target volume and/or risk volume comprises a bone structure and/or a body region located directly adjacent to a bone structure, an improved identification of the target volume and/or risk volume is thus possible.

At least one embodiment provides that the bone structures are differentiated from each other in a skull base region of the patient.

Precisely the small bone structures in the skull base region can be differentiated particularly well from each other in the spectrally resolved CT measurement data corrected by the beam hardening correction.

At least one embodiment provides that the CT measurement data comprises a first CT measurement data set and a second CT measurement data set, wherein the first CT measurement data set has been acquired by a higher energy threshold of the quantum counting X-ray detector than the second CT measurement data set, the processing of the CT measurement data comprises the creation of a weighted combination of the first CT measurement data set and the second CT measurement data set, wherein combined CT measurement data is generated and the identification of the target volume and/or risk volume takes place in the combined CT measurement data.

The procedure described in this embodiment can also be referred to as photon weighting. The first CT measurement data set and the second CT measurement data set are acquired in particular by different configurations of the quantum counting X-ray detector with regard to the energy thresholds. That the first CT measurement data set has been acquired by a higher energy threshold of the quantum counting X-ray detector than the second CT measurement data set can in particular signify that on average the first CT measurement data set has been acquired at higher energy thresholds than the second CT measurement data set. The first CT measurement data set therefore advantageously has information about higher-energy photons than the second CT measurement data set. The first CT measurement data set and the second CT measurement data set in particular cover the same field of view.

The combined CT measurement data generated by photon weighting, in particular, is particularly well-suited to the identification of the target volume and/or risk volume. The information about different photon energies from the first CT measurement data set and the second CT measurement data set can be particularly advantageously combined by suitable selection of the weighting factors such that improved identification of the target volume and/or risk volume in the combined CT measurement data is possible. Weighting factors for the formation of the weighted combination can be generated in subsequent processing based on the content of the first CT measurement data set and/or second CT measurement data set. As described in more detail hereinafter, the weighting factors can be determined by rough pre-segmentation of the CT measurement data. Alternatively, or additionally, it is also conceivable that weighting factors are obtained by a machine learning method, for example, an artificial neural network, by which combined CT measurement data that is particularly suitable for the planning of the irradiation can be generated.

At least one embodiment provides that the processing of the CT measurement data comprises the extraction of information for a beam hardening correction from the first CT measurement data set, and a beam hardening correction of the combined CT measurement data based on the extracted information, wherein the identification of the target volume and/or risk volume takes place in the combined CT measurement data corrected by the beam hardening correction.

In such a way, the information from the first CT measurement data set, which is particularly characterized by higher-energy photons than the second CT measurement data set, can be used in a particularly suitable manner for the beam hardening correction.

At least one embodiment provides that the creation of the weighted combination of the first CT measurement data set and of the second CT measurement data set takes place using spatially varying weighting factors.

In this way, a weighting factor other than for a second spatial point of the CT measurement data is particularly used for the creation of the weighted combination at a first spatial point of the CT measurement data. The weighting factors can, for example, vary over different body regions of the patient.

At least one embodiment provides that the processing of the CT measurement data initially comprises a rough identification of the target volume and/or risk volume, wherein the spatially varying weighting factors are defined by the roughly segmented target volume and/or risk volume and then a fine identification of the target volume and/or risk volume takes place in the combined CT measurement data.

Thus, for example, a different weighting factor can be set for the target volume and/or risk volume than for the body regions surrounding the target volume and/or risk volume. The rough identification of the target volume and/or risk volume therefore serves advantageously to determine the weighting factors by which a particularly advantageous weighting of the first CT measurement data set and second CT measurement data set can take place such that the fine identification of the target volume and/or risk volume can take place in particularly suitably weighted combined CT measurement data.

At least one embodiment provides that the acquisition of the CT measurement data comprises the acquisition of high-resolution CT measurement data by the quantum counting X-ray detector, wherein a high-resolution mode of the quantum counting X-ray detector is used for the acquisition of the high-resolution CT measurement data, wherein in the high-resolution mode each pixel of the quantum counting X-ray detector is counted separately.

Typically, the use of the quantum counting X-ray detector intrinsically results in an increase in the resolution compared to conventional CT acquisitions as individual detector elements, also referred to as detector pixels, of the quantum counting X-ray detector must be smaller than detector elements of conventional CT detectors as separating layers between individual pixels of the quantum counting X-ray detector, which reduce the quantum efficiency at a higher pixel resolution, are unnecessary. At the same time, the problem of crosstalk between adjacent detector pixels, which typically impedes a reduction in the size of the detector pixels of conventional CT detectors, is not customarily found in the quantum counting X-ray detector.

In principle, a high resolution of the CT measurement data can thus be achieved by the use of the quantum-counting X-ray detector in all spatial directions (x, y, z) and over the entire field of view, even when using a large bore system. The resolution of the acquired CT measurement data typically depends on the number of pixels of the quantum counting X-ray detector for which the counting pulses are jointly counted. In a standard resolution mode of the quantum counting X-ray detector, typically a plurality of pixels of the quantum counting X-ray detector are jointly counted, for example, a pixel matrix of 2×2 pixels or a different type of interconnection of pixels. The proposed use of the high-resolution mode (ultra-high resolution mode, UHR mode), in which each pixel of the quantum counting X-ray detector is counted separately, can result in a particularly high resolution of the CT measurement data. This particularly high-resolution CT measurement data can then be used particularly advantageously in the planning of the irradiation of the patient.

At least one embodiment provides that the processing of the CT measurement data comprises a calculation of a spatially resolved distribution of a quantitative material coefficient from the high-resolution CT measurement data and the provision of the result data comprises a provision of the spatially resolved distribution of the quantitative material coefficient to the interface.

The high-resolution CT measurement data can be included particularly advantageously in the calculation of the quantitative material coefficient for bone tissue. The high resolution of the CT measurement data can, for example, enable improved differentiation between different bone densities of the bone tissue.

At least one embodiment provides that the high-resolution CT measurement data is included in unaltered form in the calculation of the spatially resolved distribution of the quantitative material coefficient for a bone tissue of the patient and the high-resolution CT measurement data is included in the calculation of the spatially resolved distribution of the quantitative material coefficient for a soft tissue of the patient in a reduced resolution.

This approach is based on the consideration that particularly for calculating the spatially resolved distribution of the quantitative material coefficient for the bone tissue, a higher resolution is expedient than for the soft tissue. The reason for this is that typically finer structures are distinguishable in the bone tissue than in the soft tissue. It is therefore often sufficient for the resolution of the high-resolution CT measurement data for the calculation of the spatially resolved distribution of the quantitative material coefficient for the soft tissue to be reduced. According to at least one embodiment, the reduced resolution of the high-resolution CT measurement data is generated by filtering the high-resolution CT measurement data using a filter kernel.

At least one embodiment provides that the calculation of the spatially resolved distribution of the quantitative material coefficient comprises a calculation of a spatially resolved distribution of a stopping power from the high-resolution CT measurement data and the provision of the result data comprises the provision of the spatially resolved distribution of the stopping power for the planning of particle irradiation of the patient.

Particle irradiation takes place in particular by protons, helium ions or carbon ions. As a high degree of accuracy is typically necessary for dose calculation in the case of particle irradiation, the spatially resolved distribution of the stopping power for the planning of particle irradiation can be calculated particularly advantageously by the high-resolution CT measurement data.

At least one embodiment provides that the spatially resolved distribution of the quantitative material coefficient is calculated from the high-resolution CT measurement data for at least one of the following body regions of the patient: an eye region of the patient, a body region described by the course of the trigeminal nerve of the patient, a skull base of the patient, a lung region of the patient.

The high-resolution CT measurement data can namely be used particularly advantageously for the planning of the irradiation of body regions for which a particularly high degree of accuracy is necessary. Precisely the connection with the use of a particularly precise irradiation of the aforementioned body regions, for example, a particle irradiation or a brachytherapy irradiation, is advantageously possible here. By using the high-resolution CT measurement data, namely, for example, the influence of small bone structures can be advantageously considered with the particularly precise irradiation.

At least one embodiment provides that the acquisition of the CT measurement data comprises the acquisition of spectrally resolved and temporally resolved CT measurement data resulting from acquisition by the quantum counting X-ray detector, the processing of the CT measurement data comprises the calculation of a spatially resolved and temporally resolved distribution of a quantitative material coefficient from the spectrally resolved and temporally resolved CT measurement data and the provision of the result data comprises the provision of the spatially resolved and temporally resolved distribution of the quantitative material coefficient to the interface.

Temporally resolved CT measurement data is often important for the planning of the irradiation of the patient to be able to take into account a movement of the patient, in particular a cyclic respiratory movement in planning. This can be particularly important if the target volume is in the proximity of organs, for example, the liver, which undergo particularly strong movement with the respiratory movement.

By using the quantum counting X-ray detector for acquisition of the CT measurement data, it is possible to ensure that spectrally resolved CT measurement data can also be dynamically acquired over the course of the respiratory movement of the patient. This spectrally resolved CT measurement data can have a full temporal and spatial coherence over the course of the respiratory movement of the patient. In this way, the aforementioned dual-energy application can be advantageously employed in the processing of the spectrally resolved and temporally resolved CT measurement data. For example, over the course of the respiratory movement of the patient, suitably determined tissue of the patient can be highlighted in the CT measurement data or a time-resolved dosimetry, in particular for a target volume located in the lung for a particle therapy, is conceivable. The removal of a contrast enhancement (contrast removal) or a beam hardening correction can also take place in the temporally resolved CT measurement data.

At least one embodiment provides that the spectrally resolved and temporally resolved CT measurement data is acquired from at least one of the following body regions of the patient: a liver region of the patient, a pancreas region of the patient, a thorax region of the patient.

In particular, in the case of particularly contrast-enhanced imaging of these body regions, the spectrally resolved and temporally resolved CT measurement data can provide a particularly advantageous basis for the planning of irradiation.

At least one embodiment provides that the acquisition of the CT measurement data of the patient comprises the acquisition of the CT measurement data by the CT device having the quantum counting X-ray detector, wherein during the acquisition of the CT measurement data, a detector parameter of the quantum counting X-ray detector is changed.

The fact that a detector parameter of the quantum counting X-ray detector is changed during the acquisition of the CT measurement data in particular means that at a first instant of the acquisition of the CT measurement data, the quantum counting X-ray detector is operated with a different setting of the detector parameter than at a second instant of the acquisition of the CT measurement data. The detector parameter can be changed for different sections of the acquisition of the CT measurement data. A dynamic continuous changing of the detector parameter during the acquisition of the CT measurement data is also conceivable.

Through the static or dynamic changing of the detector parameter during data acquisition, CT measurement data, which is particularly suitable for use in the planning of the irradiation of the patient, can be acquired. Possible applications are described in more detail in the following paragraphs. At this point, three particularly suitable applications should be mentioned:

The resolution of the quantum counting X-ray detector can be specifically increased for the acquisition of the CT measurement data in a body region in which the boundaries of an organ for contouring are expected.

The detector parameter can be adjusted such that the sensitivity and/or the soft tissue contrast in a body region in which the presence of a contrast media is to be expected is increased.

In a body region in which the presence of a bone tissue is to be expected, the detector parameter can be adjusted such that an improved decomposition of the bone materials and/or a reduction of beam hardening artefacts can be achieved.

The aforementioned detector parameter can also be adapted after the acquisition of the CT measurement data for the reconstruction of the CT measurement data. Thus, a spatial variation in the resolution and/or energy thresholds for the reconstruction of the CT measurement data is conceivable. It is also conceivable that strips of detector elements of the quantum counting X-ray detector can be set with different detector parameters. This can enable specific reconstructions for a spiral acquisition. It is also conceivable that, based on the acquisition protocol and/or a positioning of the target volume and/or risk volume for specific regions of the quantum counting X-ray detector, only fixed detector parameters are used. This fixing of the detector parameters can vary with regard to the rotation of the detector-emitter system and/or a change in acquisition along the z-position.

At least one embodiment provides that during the acquisition of CT measurement data, an energy threshold of the quantum counting X-ray detector is changed.

In particular, an energy threshold of the quantum counting X-ray detector or else a plurality of energy thresholds of the quantum counting X-ray detector can be changed during the acquisition of the CT measurement data. If a plurality of energy thresholds of the quantum counting X-ray detector are changed during the acquisition of the CT measurement data, particularly at a first instant of the acquisition of CT measurement data, the quantum counting X-ray detector is operated with a set of energy thresholds other than at a second instant of the acquisition of CT measurement data. Different photon energies can be set in keV as energy thresholds. The different energy thresholds can, for example, be set as photon energy, as voltage or as current.

By adjusting the energy threshold, the quantum counting X-ray detector can be set in such a manner that the CT measurement data is acquired in a particularly suitable manner for the planning of the irradiation, for example, locally having a particularly suitable contrast between different types of tissue for the identification of the target volume and/or risk volume.

At least one embodiment provides that during the acquisition of the CT measurement data, a resolution of the quantum counting X-ray detector is changed with regard to a combination of pixels of the quantum counting X-ray detector.

In this way, the quantum counting X-ray detector can be operated with a higher resolution at a first instant of the acquisition of the CT measurement data than at a second instant of the acquisition of the CT measurement data. At the first instant, in particular fewer pixels of the quantum counting X-ray detector are therefore jointly counted than at the second instant.

It is particularly expedient for the application to be carried out in such a way that high-resolution CT measurement data is acquired from the bone tissue of the patient, while low-resolution CT measurement data is acquired from the soft tissue of the patient. Furthermore, a higher resolution of the CT measurement data in the region of the target volume and/or risk volume than in the rest of the body of the patient is also expedient.

Furthermore, it is conceivable that a photon flux is changed during the acquisition of the CT measurement data. The quantum counting X-ray detector can particularly be adapted by adapting a bit depth of the transmission to the changed photon flux. Thus, an expected photon flux, in particular according to an adapted modulation of the X-ray tubes, can be used as an input parameter for the adaptation of the bit depth. For example, when a maximum expected count rate on the quantum-counting X-ray detector is known, the bit depth of the transmission can be correspondingly throttled. If, for example, a maximum photon flux is expected, the number of threshold values and/or detector lines and/or items of information for transmission can thus be increased by way of individual detector pixels. The photon flux can only be changed in at least one of the three spatial directions (x, y, z). The advantageous application is conceivable, for example, that in the vicinity of the target volume of the irradiation, the resolution of the quantum-counting X-ray detector is increased and at the same time a particularly high dose rate is set for acquisition from this region. In this way, there can be a sufficient dose for the size of the pixels of the quantum counting X-ray detector.

Furthermore, it is also conceivable that a linear correction parameter of the quantum counting X-ray detector is changed during the acquisition of the CT measurement data.

Different ways in which the detector parameter is changed during the acquisition of the CT measurement data are conceivable.

According to at least one embodiment, CT measurement data is respectively acquired with a possible suitable setting of the detector parameter for different body regions.

According to at least a first embodiment, the detector parameter of the quantum counting X-ray detector is changed during the acquisition of the CT measurement data such that for an acquisition of the CT measurement data at a first z-position along a longitudinal direction of the patient, a first setting of the detector parameter is set and for an acquisition of the CT measurement data at a second z-position along the longitudinal direction of the patient, a second setting of the detector parameter is set.

According to at least a second embodiment, the detector parameter of the quantum counting X-ray detector is changed during the acquisition of the CT measurement data such that for an acquisition of the CT measurement data at a first rotational position of a detector-emitter system of the CT device, a first setting of the detector parameter is set and for an acquisition of the CT measurement data at a second rotational position of the detector-emitter system of the CT device, a second setting of the detector parameter is set.

According to at least a third embodiment, the detector parameter of the quantum counting X-ray detector is changed during the acquisition of the CT measurement data such that for an acquisition of the CT measurement data of a first body region of the patient, a first setting of the detector parameter is set and for an acquisition of the CT measurement data of a second body region of the patient, a second setting of the detector parameter is set.

In the following embodiments, the possibility is described in more detail of the first setting of the detector parameter being set for the acquisition of the CT measurement data of the first body region of the patient and the second setting of the detector parameter being set for the acquisition of the CT measurement data of the second body region of the patient. The embodiments can largely also be applied to the other possibilities.

At least one embodiment provides that the first body region and the second body region are established by existing medical image data of the patient and/or using an Atlas database before the acquisition of the CT measurement data.

There may already be a contour of an organ structure for the existing medical image data of the patient. The contour of the organ structure can be used in establishing the first body region and the second body region. It is also conceivable that the contour of the organ structure is established on the basis of the information contained in the Atlas database. By this approach, a detector parameter other than for the acquisition of the remaining CT measurement data can be set for the acquisition of the CT measurement data from the organ structure. According to at least one embodiment, the first body region comprises a target volume of the irradiation and the second body region comprises a body region outside the target volume of the irradiation.

At least one embodiment provides that the first body region is embodied such that it is positioned in a beam region for the irradiation of the patient, and the second body region is embodied such that it is positioned outside a beam region for the irradiation of the patient.

The beam region is known in particular from beam settings of the radiotherapy device, which are established by an existing irradiation plan.

At least one embodiment provides that the first body region and the second body region are embodied such that for the irradiation of the patient a higher radiation dose is provided for the first body region than for the second body region.

A known three-dimensional dose distribution from an existing irradiation plan can be used in this way as input information for the establishment of the detector parameter. The detector parameter can then be established in such a way that particularly for an optimization and/or adjustment of the existing irradiation plan, suitable CT measurement data can be acquired. This procedure is based in particular on the consideration that for the first body region, for which a higher radiation dose is provided, more precise imaging is necessary than for the second body region, for which a lower radiation dose is provided. It is also conceivable that the CT measurement data must display greater precision for those body regions in which there is a steep dose gradient, for example, close to the Bragg peak for a particle therapy or close to a position of brachytherapy applicators or in the vicinity of the target volume and/or risk volume.

At least one embodiment provides that during the acquisition of the CT measurement data, the detector parameter of the quantum counting X-ray detector is changed such that for the acquisition of the CT measurement data from the first body region of the patient, a higher resolution of the quantum counting X-ray detector is set than for the acquisition of the CT measurement data from the second body region of the patient.

This advantageous procedure is based on the consideration that higher resolution CT measurement data is more expedient for the first body region than for the second body region.

Alternatively, or in addition, it is also conceivable that external camera data, for example, 3-D camera data, is used to establish the body region, for example, the neck-shoulder region, in which the detector parameter is to be adjusted for acquisition by the quantum counting X-ray detector.

At least one embodiment provides that the interface acquires further measurement data which is acquired via an imaging device of a radiotherapy device used for the irradiation of the patient, wherein the result data is set in relation to the further measurement data for the planning of the irradiation of the patient.

By using the quantum counting X-ray detector for the acquisition of CT measurement data, the result data can be set in relation to the further measurement data with greater ease. For example, a simpler scatter correction is possible.

At least one embodiment provides that the imaging device of the radiotherapy device used for the irradiation of the patient likewise has a quantum counting X-ray detector, wherein the result data is set in relation to the further measurement data using a specific information content of the CT measurement data and the further CT measurement data resulting from the use of the quantum counting X-ray detector in the acquisition of the CT measurement data and the further measurement data.

Using the additional specific information content, the CT measurement data can be set in relation to the further measurement data with particular ease.

At least one embodiment provides that the CT measurement data comprises at least two CT measurement data sets acquired at different instants, wherein the at least two CT measurement data sets are registered using the specific information content of the CT measurement data resulting from the use of the at least one quantum counting X-ray detector in the acquisition of the CT measurement data, wherein the registered at least two CT measurement data sets are made available to the interface.

In this way, a registration of the at least two CT measurement data sets can be improved. This can be expedient for special CT applications, for example, perfusion imaging and/or functional imaging, in particular the lung of the patient.

In the following two embodiments, two more applications are described in which a contrast media-based acquisition of the CT measurement data can be suitably performed and evaluated by the quantum counting X-ray detector: at least the first embodiment provides that during the acquisition of the CT measurement data, a contrast media has been used, wherein the processing of the CT measurement data comprises a material decomposition of the CT measurement data in tissue having contrast media, and comprises other tissue using the specific information content of the CT measurement data resulting from the use of the at least one quantum counting X-ray detector in the acquisition of the CT measurement data. At least the second embodiment provides that during the acquisition of the CT measurement data a contrast media has been used, wherein the processing of the CT measurement data comprises the creation of a virtual non-contrasted CT image using the specific information content of the CT measurement data resulting from the use of the at least one quantum counting X-ray detector in the acquisition of the CT measurement data. Here, k-edge imaging can be used to create the virtual non-contrasted image.

Finally, it is also conceivable that the processing of the CT measurement data comprises the detection and/or quantification of metal nanoparticles which are located in the patient to increase the effect of the irradiation of the patient, using the specific information content of the CT measurement data resulting from the use of the at least one quantum counting X-ray detector in the acquisition of the CT measurement data.

The arithmetic unit according to at least one embodiment of the invention comprises at least one calculation module, wherein the arithmetic unit is designed to perform a method according to the at least one embodiment of the invention.

In this way, the arithmetic unit is designed to perform a method for the provision of result data, which is suitable for use in the planning of the irradiation of a patient. The calculation module is designed for the acquisition of CT measurement data of the patient which has been acquired via a CT device having a quantum counting X-ray detector, for the processing of the CT measurement data, wherein a specific information content of the CT measurement data resulting from the use of the quantum counting X-ray detector in the acquisition of the CT measurement data is taken into account for the processing of the CT measurement data, wherein for the processing of the CT measurement data, result data is generated which is suitable for use in the planning of the irradiation of the patient, and for the provision of result data to an interface such that the result data can be used for the planning of the irradiation of the patient.

For the most part, the components of the arithmetic unit can be embodied in the form of software components. In principle, however, these components can also be partly realized, in particular in the case of particularly rapid calculations, in the form of software-supported hardware components, for example, FPGAs or the like. Likewise, the required interfaces can be designed as software interfaces, for example, if all that is involved is a transfer of data from other software components. However, they can also be designed as hardware interfaces, which are controlled by suitable software. Of course, it is also conceivable that a plurality of the aforementioned components is realized in a combined manner in the form of an individual software component and/or software-supported hardware component.

The CT device according to at least one embodiment of the invention comprises the arithmetic unit according to at least one embodiment of the invention.

The arithmetic unit can be designed to transmit control signals to the CT device and/or to receive and/or process control signals in order to perform a method according to at least one embodiment of the invention. The arithmetic unit can be incorporated into the CT device. The arithmetic unit can also be installed separately from the CT device. The arithmetic unit can be connected to the CT device.

The computer program product according to at least one embodiment of the invention can be loaded directly into the memory of a programmable arithmetic unit and has program code to perform a method according to at least one embodiment of the invention if the computer program product is performed in the arithmetic unit. The computer program product can be a computer program or comprise a computer program. As a result, the method according to at least one embodiment of the invention can be performed quickly, repeated identically and robustly. The computer program product is configured such that it can perform the steps according to at least one embodiment of the invention via the arithmetic unit. The arithmetic unit must in each case meet the requirements such as, for example, a corresponding working memory, a corresponding graphics card or a corresponding logic unit such that the respective steps can be carried out efficiently. The computer program product is stored, for example, on a machine-readable medium or on a network or server from where it can be loaded into the processor of a local arithmetic unit. Furthermore, control information of the computer program product can be stored on an electronically readable data carrier. The control information of the electronically readable data carrier can be designed such that it performs a method according to at least one embodiment of the invention when the data carrier is used in an arithmetic unit. The computer program product can thus also represent the electronically readable data carrier. Examples of electronically readable data carriers are a DVD, a magnetic tape, a hard disk or a USB stick on which electronically readable control information, in particular software (cf. above), is stored. If this control information (software) is read by the data carrier and stored in a control system and/or arithmetic unit, one or more embodiments according to the invention of the previously described method can be performed. One or more embodiments of the invention can thus also originate from the aforementioned machine-readable medium and/or the aforementioned electronically readable data carrier.

The advantages of the arithmetic unit according to at least one embodiment of the invention, of the CT device according to at least one embodiment of the invention and of the computer program product according to at least one embodiment of the invention essentially correspond to the advantages of the method according to at least one embodiment of the invention described in detail previously. Features, advantages or alternative embodiments mentioned here are likewise also applicable to the other embodiments and vice versa. In other words, the subject claims can also be developed with the features, which are described or claimed in connection with a method. The corresponding functional features of the method are embodied by corresponding subject modules, in particular by hardware modules.

FIG. 1 shows a CT device 1 according to the embodiments of the embodiments of the invention with an arithmetic unit 35 according to the embodiments of the embodiments of the invention.

The CT device 1 has a gantry 20, a tunnel-shaped opening 9, a patient support device 10 and a command device 30. The gantry 20 has a stationary support frame 21 and a rotor 24. The rotor 24 is arranged rotatably on the stationary support frame 21 by a rotary bearing device around a rotational axis relative to the stationary support frame 21. A patient 13 can be inserted into the tunnel-shaped opening 9. An acquisition region 4 is located in the tunnel-shaped opening 9. A region of the patient 13 for imaging, in particular the field of view, can be positioned in the acquisition region 4 in such a way that electromagnetic radiation 27 can pass from a radiation source 26 to the region for imaging, and after interaction with the region for imaging, to a quantum counting X-ray detector 28. The patient support device 10 has a support table 11 and a transfer plate 12 for supporting the patient 13. The transfer plate 12 is movably arranged on the support table 11 relative to the support table 11 such that the transfer plate 12 can be introduced into the acquisition region 4 in a longitudinal direction of the transfer plate 12.

The CT device 1 is designed for the acquisition of CT measurement data based on electromagnetic radiation 27. The CT device 1 comprises a CT measurement data acquisition unit with the radiation source 26, in particular an X-ray source, and the quantum counting X-ray detector 28. The radiation source 26 is arranged on the rotor 24 and designed for the emission of radiation 27, in particular X-ray radiation, with radiation quanta 27. The quantum counting X-ray detector 28 is arranged on the rotor 24 and designed for the detection of radiation quanta 27. The radiation quanta 27 can pass from the radiation source 26 to the region of the patient 13 for imaging and, following interaction with the region for imaging, impinge on the quantum counting X-ray detector 28. In this way, CT measurement data of the region for imaging can be acquired via the acquisition unit.

A command device 30 is designed to receive and process the CT measurement data acquired from the acquisition unit. The command device 30 is designed to control the CT device 1.

The CT device 1 has an input unit 38 and a display unit 39 which are each connected to the command device 30. The input unit 38 is designed for the input of control system information, for example, image reconstruction parameters and/or examination parameters. The display unit 39 is particularly designed for the display of the acquired CT measurement data, in particular of CT image data reconstructed from the CT measurement data.

The CT device 1 shown can of course comprise further components, which usually have CT devices 1. A general mode of operation of a CT device 1 is also known to a person skilled in the art, dispensing with the need for a detailed description of the further components.

The arithmetic unit 35 shown comprises at least one calculation module 36. The CT device 1 is thus designed together with the computing unit 35 for performing a method according to the embodiments of the invention. The arithmetic unit can acquire the CT measurement data from the command device 30 of the CT device 1. For this purpose, the computing unit 35 is advantageously connected to the control device 30 of the CT device 11 with regard to a data exchange. Alternatively, the arithmetic unit 35 can also be designed solely for performing a method according to the embodiments of the invention. For this purpose, the computer unit 35 typically loads the CT measurement data from a database and/or retrieves the same from the CT device 1.

Figure 2:
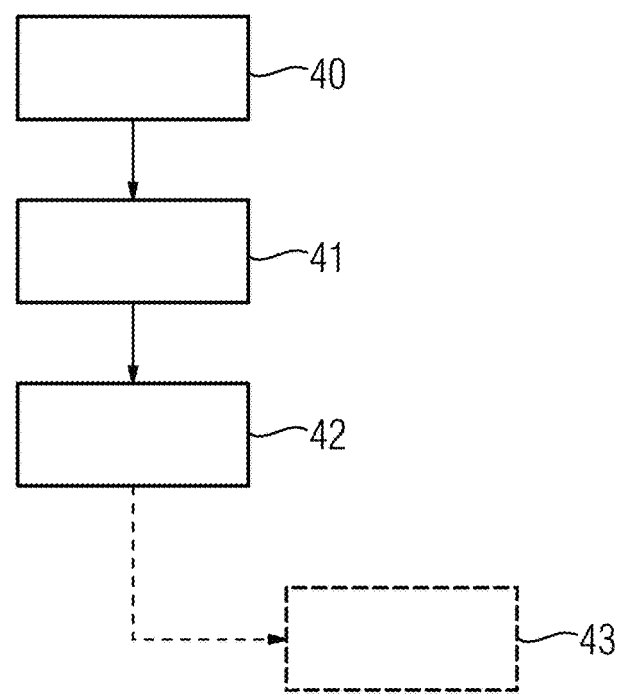
FIG. 2: A flow chart of a first embodiment of a method according to at least one embodiment of the invention.

FIG. 2 shows a flow chart of a first embodiment of a method according to the embodiments of the invention for the provision of result data, which is suitable for use in the planning of an irradiation of a patient.

In a step 40, CT measurement data of the patient, which has been acquired via a CT device having a quantum-counting X-ray detector is acquired.

In a step 41, the CT measurement data is processed, wherein during the processing of the CT measurement data, a specific information content of the CT measurement data resulting from the use of the quantum counting X-ray detector in the acquisition of the CT measurement data is taken into account, wherein result data which is suitable for use in the planning of the irradiation of the patient is generated during the processing of the CT measurement data.

In a step 42, the result data is provided to an interface such that the result data can be used for the planning of the irradiation of the patient.

The method according to the embodiments of the invention can be expanded in such a way that the planning of the irradiation of the patient is carried out in a step 43, wherein the result data is retrieved from the interface and used in the planning of the irradiation of the patient.

The following description is essentially restricted to the differences in relation to the exemplary embodiment in FIG. 2, wherein reference is made to the description of the exemplary embodiment in FIG. 2 with regard to steps, which remain the same. Steps, which essentially remain the same, are always given the same reference characters.

Figure 3:
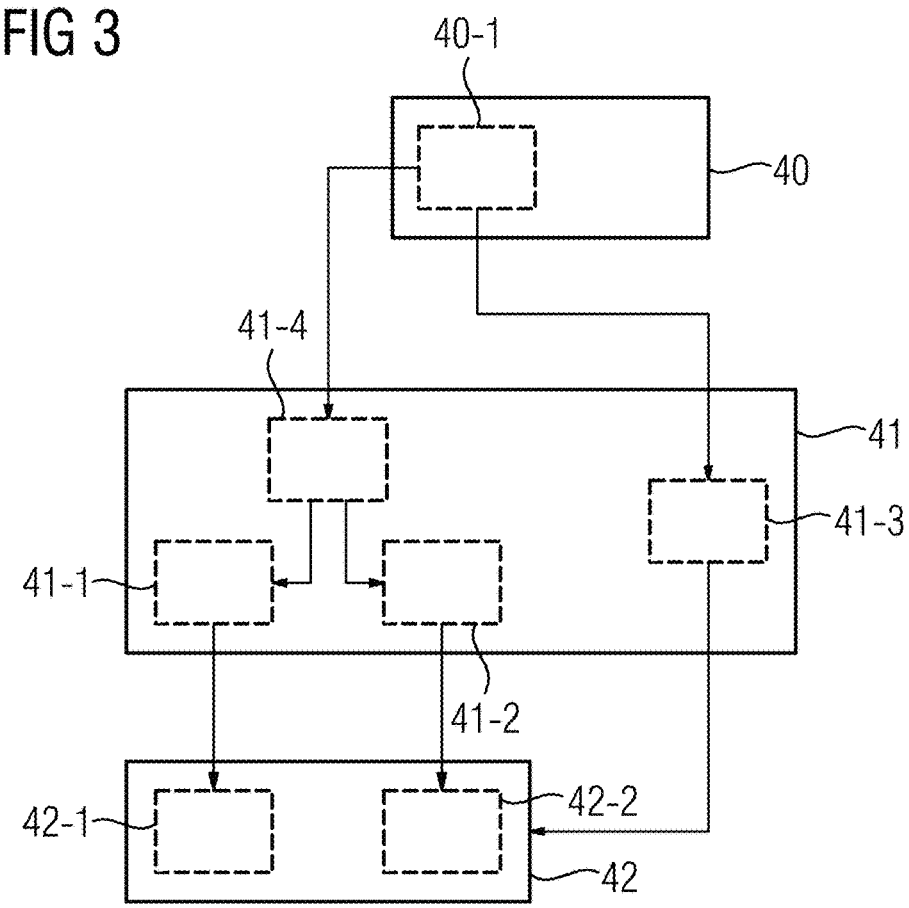
FIG. 3: A flow chart of a second embodiment of a method according to at least one embodiment of the invention.

FIG. 3 shows a flow chart of a second embodiment of a method according to the embodiments of the invention.

The acquisition of CT measurement data in the step 40 comprises the acquisition of spectrally resolved CT measurement data resulting from acquisition via the quantum counting X-ray detector in a step 40-1. Alternatively, or in addition, the acquisition of the CT measurement data may comprise the loading of previously acquired spectrally resolved CT measurement data from a database for the calculation of the spatially resolved distribution of the quantitative material coefficient. The spectrally resolved CT measurement data advantageously covers a field of view comprising, in an axial measuring layer, both the entire body of the patient and positioning aids used for supporting the patient.

The processing of the CT measurement data in the step 41 comprises a calculation of a spatially resolved distribution of a quantitative material coefficient from the spectrally resolved CT measurement data in a step 41-1. The provision of the result data comprises the provision of the spatially resolved distribution of the quantitative material coefficient to the interface in a step 42-1.

The advantageous procedure is shown in FIG. 3, characterized in that the processing of the CT measurement data comprises a calculation of two spatially resolved distributions of two different quantitative material coefficients. A first spatially resolved distribution of a first quantitative material coefficient is thus calculated in the step 41-1 and a second spatially resolved distribution of a second quantitative material coefficient from the spectrally resolved CT measurement data is calculated in a step 41-2. Accordingly, the provision of the result data in the step 42 according to FIG. 3 comprises the provision of the first spatially resolved distribution of the first quantitative material coefficient for a first dose calculation algorithm in a method step 42-1 and provision of the second spatially resolved distribution of the second quantitative material coefficient for a second dose calculation algorithm in a step 42-2. For example, the first quantitative material coefficient is an electron density and the second quantitative material coefficient is an effective core charge number. For example, the first quantitative material coefficient is an electron density and the second quantitative material coefficient is an effective atomic number. It is also conceivable that the first quantitative material coefficient and the second quantitative material coefficient are based on two base materials, which are linearly independent of each other.

The advantageous procedure is not shown in FIG. 3, characterized in that the processing of the CT measurement data comprises a separate processing of the first spatially resolved distribution of the first quantitative material coefficient and of the second spatially resolved distribution of the second quantitative material coefficient and a generation of the result data by a combination of the partial result data generated during separate processing.

The procedure is likewise illustrated in FIG. 3, characterized in that the processing of the CT measurement data in a step 41-3, in addition to the calculation of the spatially resolved distribution of the quantitative material coefficient from the spectrally resolved CT measurement data, comprises the identification of a target volume and/or risk volume in the spectrally resolved CT measurement data. In this case, the advantageous procedure is conceivable, characterized in that the spectrally resolved CT measurement data has been acquired via such recording parameters of the quantum counting X-ray detector, characterized in that the spectrally resolved CT measurement data has a particularly suitable contrast between different tissue types for the identification of the target volume and/or risk volume.

In the case shown in FIG. 3, the processing of the CT measurement data in a step 41-4 comprises a beam hardening correction of the spectrally resolved CT measurement data using spectral information contained in the spectrally resolved CT measurement data, wherein the spatially resolved distribution of the quantitative material coefficient is calculated from the spectrally resolved CT measurement data corrected by the beam hardening correction. It goes without saying that, contrary to the procedure shown in FIG. 3, the quantitative material coefficient can also be calculated directly from the CT measurement data, which has not been corrected.

Figure 4:
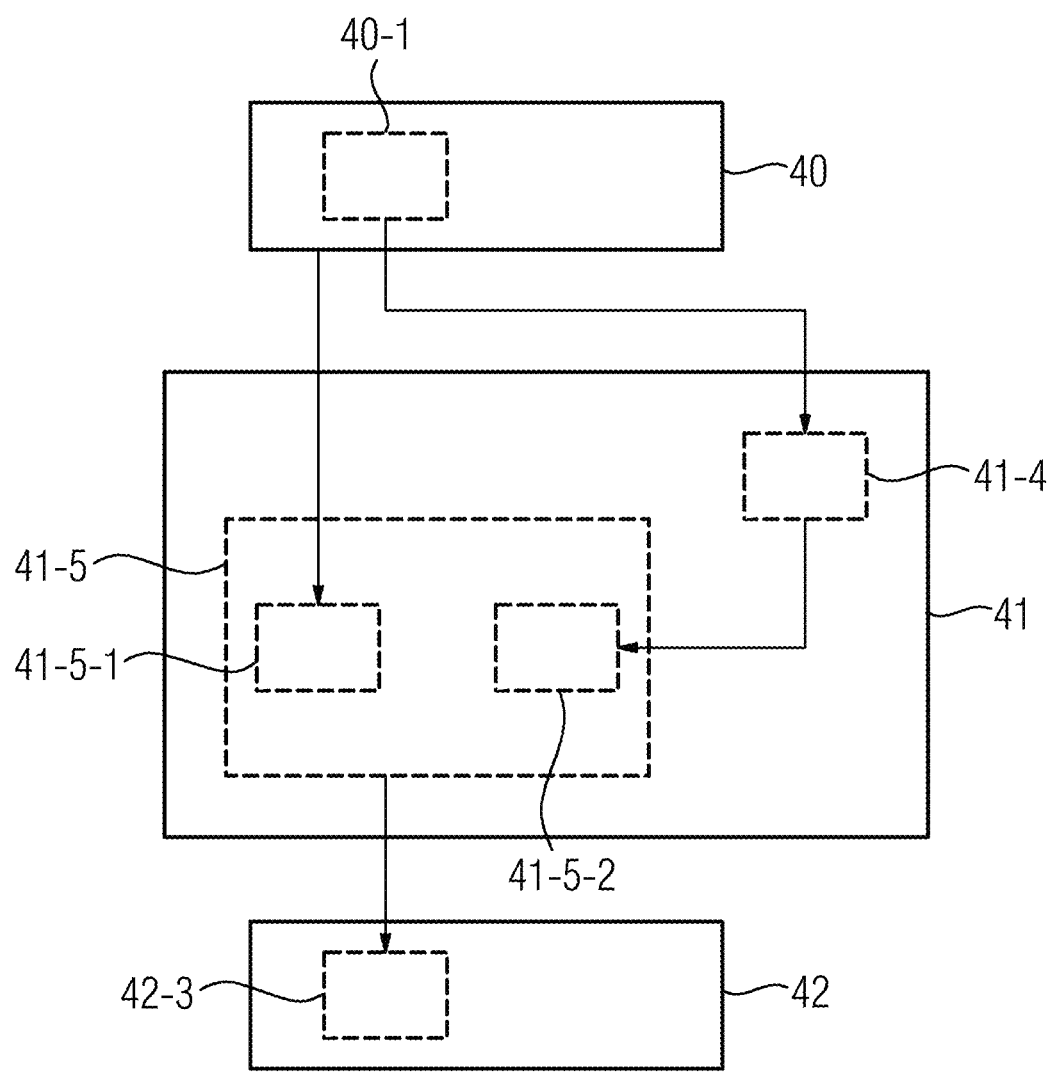
FIG. 4: A flow chart of a third embodiment of a method according to at least one embodiment of the invention.

FIG. 4 shows a flow chart of a third embodiment of a method according to the embodiments of the invention.

In the case shown in FIG. 4, the processing of the CT measurement data in a step 41-5 comprises an identification of a target volume and/or risk volume in the CT measurement data. In this way, the provision of the result data comprises the provision of the identified target volume and/or risk volume to the interface in a step 42-3.

In the case shown in FIG. 4, the identification of the target volume and/or risk volume in a step 41-5-1 comprises the differentiation of a tissue of the target volume and/or risk volume from the surrounding tissue, wherein the differentiation of the tissue of the target volume and/or risk volume from the surrounding tissue takes place using the specific information content of the CT measurement data resulting from the use of the at least one quantum counting X-ray detector in the acquisition of the CT measurement data.

The advantageous procedure is also conceivable that the identification of the target volume and/or risk volume comprises a differentiation of adipose tissue and muscle tissue, wherein the differentiation of the adipose tissue and muscle tissue takes place using the specific information content of the CT measurement data resulting from the use of the at least one quantum counting X-ray detector in the acquisition of the CT measurement data.

Alternatively, or in addition, the procedure is also conceivable that the identification of the target volume and/or risk volume comprises a differentiation of gray matter and white matter, wherein the differentiation of gray matter and white matter takes place using the specific information content of the CT measurement data resulting from the use of the at least one quantum counting X-ray detector in the acquisition of the CT measurement data.

In addition, FIG. 4 shows the procedure that in a step 40-1 the acquisition of the CT measurement data comprises the acquisition of spectrally resolved CT measurement data resulting from acquisition via the quantum counting X-ray detector, in a step 41-4 the processing of the CT measurement data comprises a beam hardening correction of the spectrally resolved CT measurement data using spectral information contained in the spectrally resolved CT measurement data and in a step 41-5-2 the identification of the target volume and/or risk volume comprises a differentiation of bone structures in the spectrally resolved CT measurement data corrected by the beam hardening correction. Here, the bone structures are advantageously differentiated from each other in a skull base region of the patient.

Of course, the identification of the target volume and/or risk volume in the step 41-5-1 can also comprise the identification of the bone structure and/or the differentiation between gray matter and white matter and/or the differentiation of adipose tissue and muscle tissue.

Figure 5:
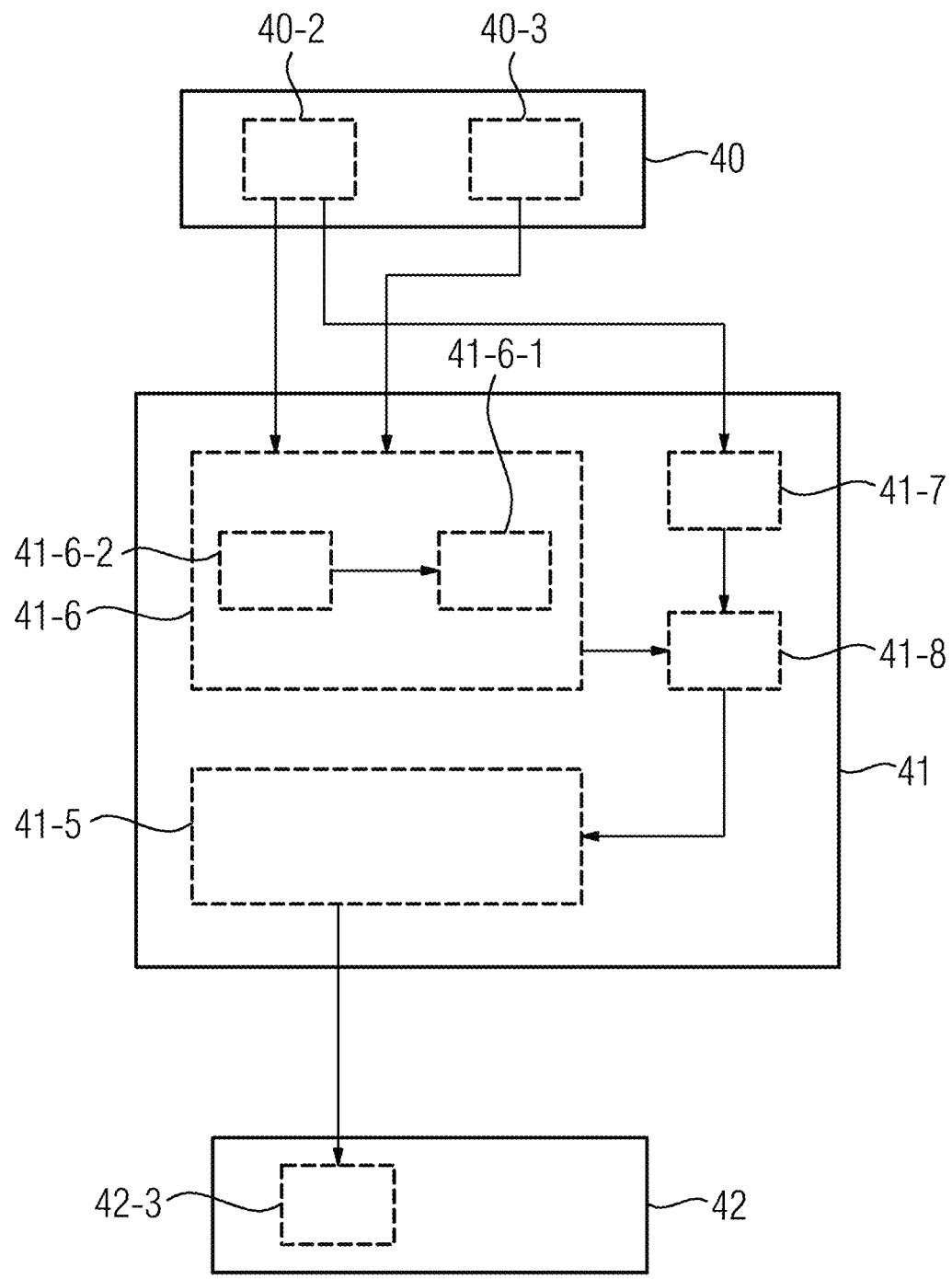
FIG. 5: A flow chart of a fourth embodiment of a method according to at least one embodiment of the invention.

FIG. 5 shows a flow chart of a fourth embodiment of a method according to the embodiments of the invention.

The procedure is illustrated in FIG. 5, characterized in that the acquisition of the CT measurement data comprises an acquisition of a first CT measurement data set in a step 40-2 and an acquisition of a second CT measurement data set in a step 40-3. In this case, the first CT measurement data set has been acquired by a higher energy threshold of the quantum counting X-ray detector than the second CT measurement data set. The processing of the CT measurement data in a step 41-6 comprises the creation of a weighted combination of the first CT measurement data set and of the second CT measurement data set, wherein combined CT measurement data is generated. In this way, the identification of the target volume and/or risk volume in the combined CT measurement data takes place in a step 41-5.

The advantageous procedure is shown in FIG. 5 in that the processing of the CT measurement data in a step 41-7 comprises the extraction of information for a beam hardening correction from the first CT measurement data set and in a step 41-8, a hardening correction of the combined CT measurement data based on the extracted information. In this way, in a step 41-5 the identification of the target volume and/or risk volume takes place in the combined CT measurement data corrected by the beam hardening correction.

Furthermore, in the step 41-6-1 the creation of the weighted combination of the first CT measurement data set and of the second CT measurement data set takes place using spatially varying weighting factors. For this purpose, in the case shown in FIG. 5, the processing of the CT measurement data in a step 41-6-2 first comprises a rough identification of the target volume and/or risk volume, wherein the spatially varying weighting factors are defined by the roughly segmented target volume and/or risk volume and then a fine identification of the target volume and/or risk volume takes place in the combined CT measurement data.

Figure 6:
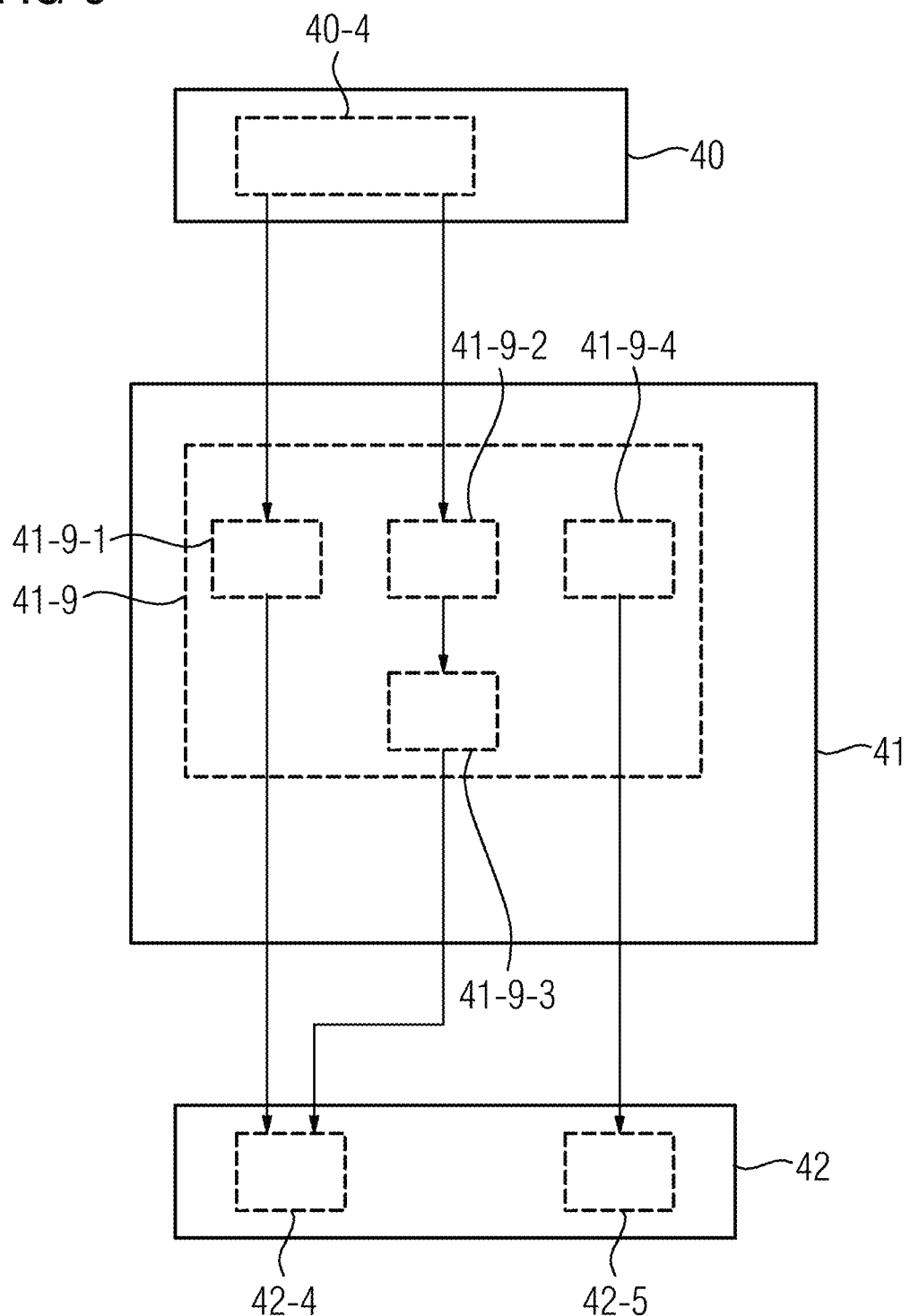
FIG. 6: A flow chart of a fifth embodiment of a method according to at least one embodiment of the invention.

FIG. 6 shows a flow chart of a fifth embodiment of a method according to the embodiments of the invention.

The acquisition of the CT measurement data according to FIG. 6 comprises the acquisition of high-resolution CT measurement data by the quantum counting X-ray detector in a step 40-4, wherein a high-resolution mode of the quantum counting X-ray detector is used for the acquisition of the high-resolution CT measurement data, wherein each pixel of the quantum counting X-ray detector is counted separately in the high-resolution mode.

In this way, in a step 41-9 the processing of the CT measurement data comprises a calculation of a spatially resolved distribution of a quantitative material coefficient from the high-resolution CT measurement data. Consequently, the provision of the result data comprises the provision of the spatially resolved distribution of the quantitative material coefficient to the interface in a step 42-4.

The advantageous procedure is shown in FIG. 6 that in a step 41-9-1 the high-resolution CT measurement data is included in the calculation of the spatially resolved distribution of the quantitative material coefficient for a bone tissue of the patient in unaltered form and in a step 41-9-3 the high-resolution CT measurement data is included in the calculation of the spatially resolved distribution of the quantitative material coefficient for a soft tissue of the patient in a reduced resolution. The reduced resolution of the high-resolution CT measurement data is generated in a step 41-9-2 by filtering the high-resolution CT measurement data using a filter kernel.

In addition, the advantageous procedure is also illustrated in FIG. 6, in a step 41-9-4, in that the calculation of the spatially resolved distribution of the quantitative material coefficient comprises a calculation of a spatially resolved distribution of a stopping power from the high-resolution CT measurement data and in a step 42-5 the provision of the result data comprises the provision of the spatially resolved distribution of the stopping power for planning the particle irradiation of the patient.

In general, the spatially resolved distribution of the quantitative material coefficient is calculated advantageously from the high-resolution CT measurement data for at least one of the following body regions of the patient:

An eye region of the patient,
A body region described by a course of the trigeminal nerve of the patient,
The skull base of the patient,
A lung region of the patient.

Figure 7:
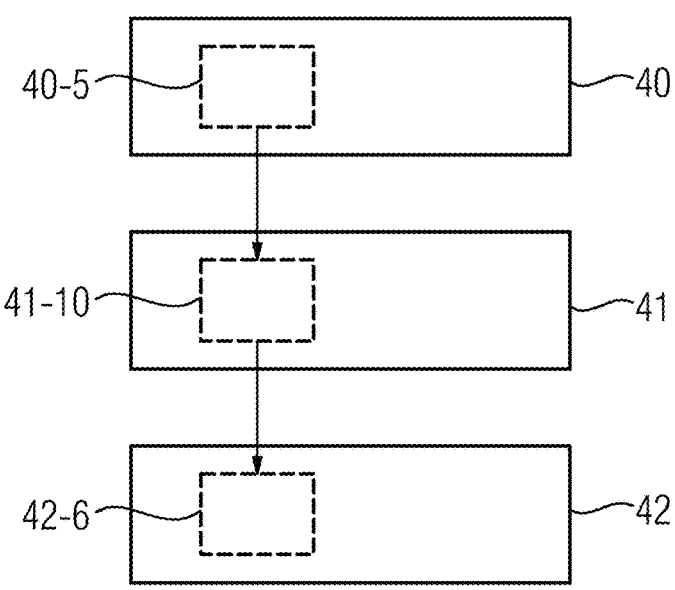
FIG. 7: A flow chart of a sixth embodiment of a method according to at least one embodiment of the invention.

FIG. 7 shows a flow chart of a sixth embodiment of a method according to the embodiments of the invention.

FIG. 7 shows the procedure in which in a step 40-5, the acquisition of the CT measurement data comprises the acquisition of spectrally resolved and temporally resolved CT measurement data resulting from the acquisition by the quantum counting X-ray detector, in a step 41-10, the processing of the CT measurement data comprises a calculation of a spatially resolved and temporally resolved distribution of a quantitative material coefficient from the spectrally resolved and temporally resolved CT measurement data and in a step 42-6, the provision of the result data comprises a provision of the spatially resolved and temporally resolved distribution of the quantitative material coefficient to the interface.

The spectrally resolved and temporally resolved CT measurement data is advantageously acquired from at least one of the following body regions of the patient:

A liver region of the patient,

A pancreas region of the patient,

A thorax region of the patient.

Figure 8:
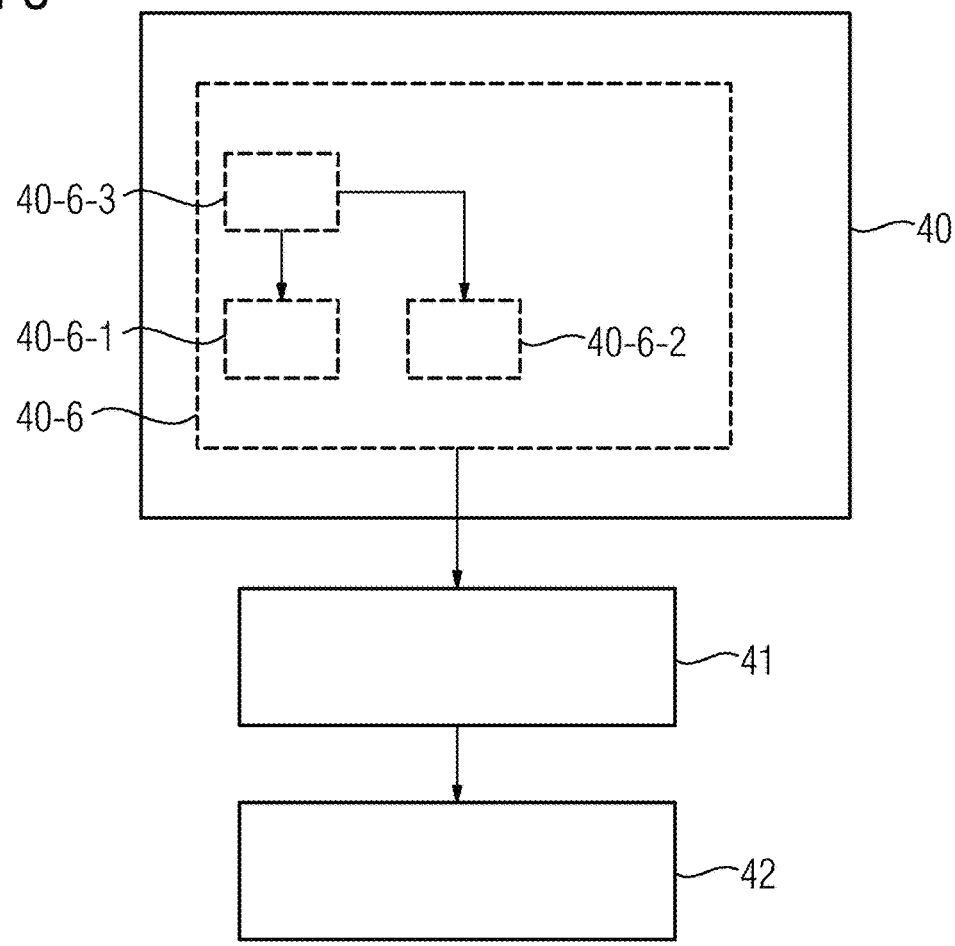
FIG. 8: A flow chart of a seventh embodiment of a method according to at least one embodiment of the invention.

FIG. 8 shows a flow chart of a seventh embodiment of a method according to the embodiments of the invention.

According to FIG. 8, in a step 40-6, the acquisition of the CT measurement data of the patient comprises the acquisition of the CT measurement data via the CT device having the quantum counting X-ray detector, wherein during the acquisition of the CT measurement data, a detector parameter of the quantum counting X-ray detector is changed.

In particular, at least one of the following detector parameters is changed during the acquisition of the CT measurement data:

An energy threshold of the quantum counting X-ray detector,

A resolution of the quantum counting X-ray detector with regard to a combination of pixels of the quantum counting X-ray detector.

In the case shown in FIG. 8, the detector parameter of the quantum counting X-ray detector is changed during the acquisition of the CT measurement data such that, in a step 40-6-1, a first setting of the detector parameter is set for an acquisition of the CT measurement data of a first body region of the patient and in a step 40-6-2, a second setting of the detector parameter is set for an acquisition of the CT measurement data of a second body region of the patient. In a step 40-6-3, the first body region and the second body region are established before the acquisition of the CT measurement data by existing medical image data of the patient and/or using an Atlas database. Advantageously, during the acquisition of the CT measurement data the detector parameter of the quantum counting X-ray detector is changed such that a higher resolution of the quantum counting X-ray detector is set for the acquisition of the CT measurement data from the first body region of the patient than for the acquisition of the CT measurement data from the second body region of the patient.

The body regions can be selected according to the following properties. In this case, any desired combination of the properties is conceivable:

The first body region comprises a target volume of the irradiation and the second body region comprises a body region located outside of the target volume of the irradiation.

The first body region is embodied such that it is positioned in a beam region during the irradiation of the patient, and the second body region is embodied such that is positioned outside a beam region during the irradiation of the patient.

The first body region and the second body region are embodied such that during the irradiation of the patient a higher radiation dose is provided for the first body region than for the second body region.

Alternatively or in addition, the procedure not shown is also conceivable that the detector parameter of the quantum counting X-ray detector is changed during the acquisition of the CT measurement data such that a first setting of the detector parameter is set for an acquisition of the CT measurement data at a first z-position along a longitudinal direction of the patient and a second setting of the detector parameter is set for an acquisition of the CT measurement data at a second z-position along the longitudinal direction of the patient.

Alternatively or in addition, the procedure not shown is also conceivable that the detector parameter of the quantum counting X-ray detector is changed during the acquisition of the CT measurement data such that a first setting of the detector parameter is set for an acquisition of the CT measurement data in a first rotational position of a detector-emitter system of the CT device and a second setting of the detector parameter is set for an acquisition of the CT measurement data in a second rotational position of the detector-emitter system of the CT device.

Figure 9:
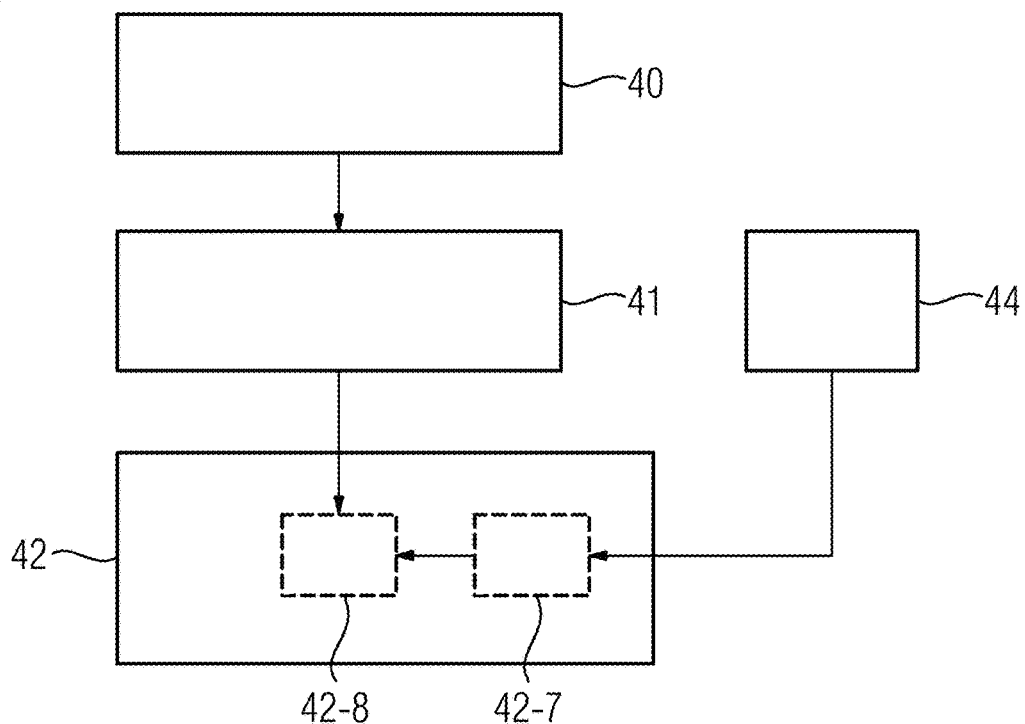
FIG. 9: A flow chart of an eighth embodiment of a method according to at least one embodiment of the invention.

FIG. 9 shows a flow chart of an eighth embodiment of a method according to the embodiments of the invention.

According to FIG. 9, in a step 42-7, the interface acquires further measurement data, which is acquired via an imaging device of a radiotherapy device used for the irradiation of the patient, wherein in a step 42-8, the result data is set in relation to the further measurement data for the planning of the irradiation of the patient. Advantageously, the imaging device of the radiotherapy device used for the irradiation of the patient likewise has a quantum counting X-ray detector, wherein the result data is set in relation to the further measurement data using a specific information content of the CT measurement data and the further CT measurement data resulting from the use of the quantum counting X-ray detector in the acquisition of the CT measurement data and the further measurement data.

Figure 10:
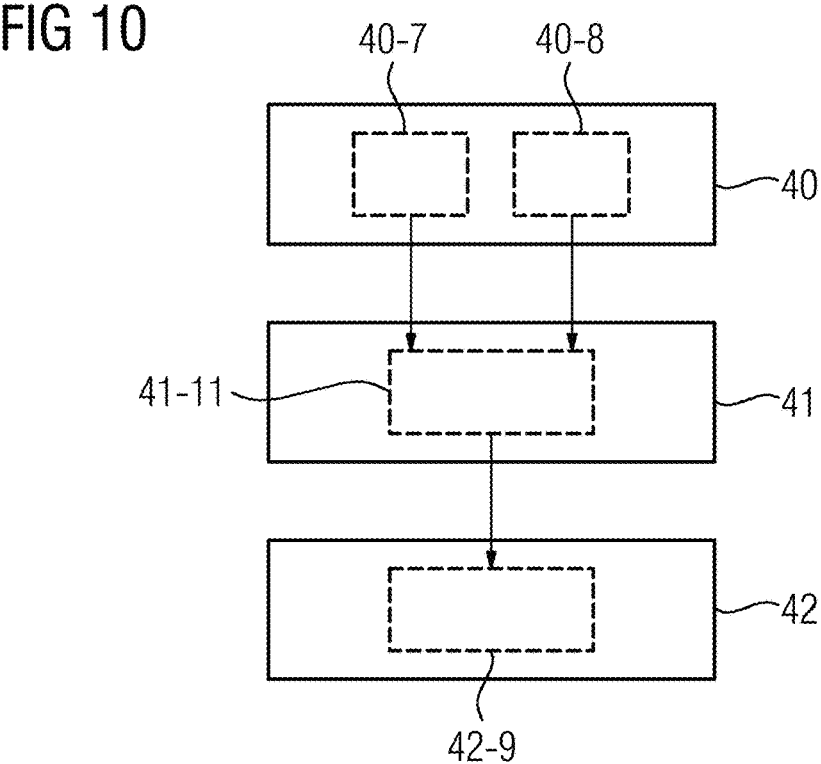
FIG. 10: A flow chart of a ninth embodiment of a method according to at least one embodiment of the invention.

FIG. 10 shows a flow chart of a ninth embodiment of a method according to the embodiments of the invention.

According to FIG. 10, a first CT measurement data set is acquired in a step 40-7, and a second CT measurement data set in a step 40-8. Both CT measurement data sets are acquired at different times. In a step 41-11, the at least two CT measurement data sets are registered using the specific information content of the CT measurement data resulting from the use of the at least one quantum counting X-ray detector in the acquisition of the CT measurement data. In a step 42-9, the registered at least two CT measurement data sets are made available to the interface.

Figure 11:
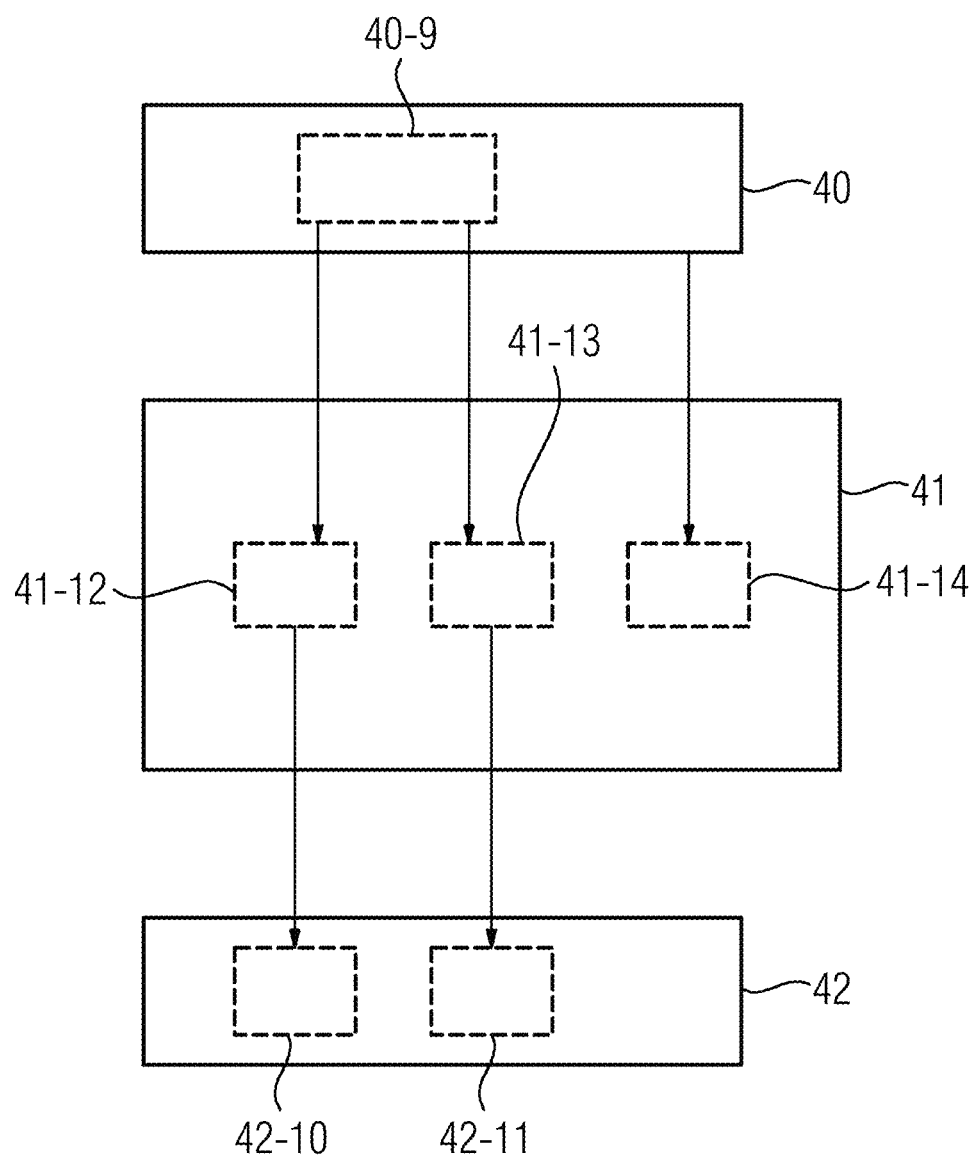
FIG. 11: A flow chart of a tenth embodiment of a method according to at least one embodiment of the invention.

FIG. 11 shows a flow chart of a tenth embodiment of a method according to the embodiments of the invention.

In the case shown in FIG. 11, in a step 40-9 a contrast media has been used during the acquisition of the CT measurement data.

According to a first application, the processing of the CT measurement data in a step 41-12 comprises a material decomposition of the CT measurement data in tissue having contrast media, and other tissue using the specific information content of the CT measurement data resulting from the use of the at least one quantum counting X-ray detector in the acquisition of the CT measurement data. The material decomposition is made available to the interface in a step 42-10.

Alternatively, or in addition, the second application can be used so that in a step 41-13 the processing of the CT measurement data comprises the creation of a virtual non-contrasted CT image using the specific information content of the CT measurement data resulting from the use of the at least one quantum counting X-ray detector in the acquisition of the CT measurement data, wherein in a step 42-11 the virtual non-contrasted CT image is provided to the interface.

Finally, the procedure is also illustrated in FIG. 11, characterized in that the processing of the CT measurement data in a step 41-14 comprises the detection and/or quantification of metal nanoparticles which are located in the patient in order to increase an effect of the irradiation of the patient, using the specific information content of the CT measurement data resulting from the use of the at least one quantum counting X-ray detector in the acquisition of the CT measurement data.

The steps of the method according to the embodiments of the invention shown in FIG. 2-11 are performed by the arithmetic unit. For this purpose, the arithmetic unit comprises the necessary software and/or computer programs, which are stored in a storage unit of the arithmetic unit. The software and/or computer programs comprise programs, which are designed to execute the method according to the embodiments of the invention when the computer program and/or the software in the arithmetic unit is executed by a processor unit of the arithmetic unit.

Although the embodiments of the invention has been illustrated and described in more detail by the preferred exemplary embodiments, the embodiments of the invention is nevertheless not restricted by the disclosed examples and other variations can be derived therefrom by a person skilled in the art, without departing from the scope of protection of the embodiments of the invention.

The invention claimed is:

1. A method for provisioning result data suitable for planning an irradiation of a patient, the method comprising:
    acquiring CT measurement data of the patient via a CT device having a quantum counting X-ray detector, the acquiring including changing a detector parameter of the quantum counting X-ray detector during the acquiring, the changing the detector parameter including changing the detector parameter of the quantum counting X-ray detector during the acquiring of the CT measurement data such that a first setting of the detector parameter is set for acquiring the CT measurement data at a first z-position along a longitudinal direction of the patient, and a second setting of the detector parameter is set for acquiring the CT measurement data at a second z-position along the longitudinal direction of the patient;
    processing the CT measurement data to generate result data suitable for the planning of the irradiation of the patient, the processing the CT measurement data based on an information content of the CT measurement data resulting from use of the quantum counting X-ray detector in the acquiring of the CT measurement data; and
    provisioning the result data to an interface for planning the irradiation of the patient.

2. The method as claimed in claim 1, further comprising:
    acquiring, via the interface, further measurement data, the further measurement data being acquired by an imaging device of a radiotherapy device used for the irradiation of the patient; and
    adjusting the result data based on the further measurement data for the planning of the irradiation of the patient.

3. The method as claimed in claim 2, wherein
    the imaging device of the radiotherapy device has a quantum counting X-ray detector,
    the adjusting the result data includes adjusting the result data based on the further measurement data using the information content of the CT measurement data and information content of the further measurement data resulting from using the quantum counting X-ray detector in the acquiring of the further measurement data.

4. The method as claimed in claim 1, wherein
    the CT measurement data includes at least two CT measurement data sets acquired at different times, and
    the method further comprises:
        registering the at least two CT measurement data sets using the information content of the CT measurement data resulting from using the quantum counting X-ray detector in the acquiring of the CT measurement data; and
        providing the at least two CT measurement data sets to the interface.

5. The method as claimed claim 1, wherein
    a contrast media is used during the acquiring of the CT measurement data, and
    the processing of the CT measurement data includes a material decomposition of the CT measurement data in tissue having the contrast media and other tissue using the information content of the CT measurement data.

6. The method as claimed claim 1, wherein
    the acquiring includes using a contrast media during the acquiring of CT measurement data, and
    the processing the CT measurement data includes creating a virtual non-contrasted CT image using the information content of the CT measurement data.

7. An arithmetic unit, comprising:
    at least one calculation module, the arithmetic unit being configured to execute the method as claimed in claim 1.

8. A CT device, comprising:
    the arithmetic unit as claimed in claim 7.

9. A non-transitory computer readable medium storing executable instructions that, when executed by one or more processors of a programmable arithmetic unit, cause the programmable arithmetic unit to execute the method as claimed in claim 1.

10. A method for provisioning result data suitable for planning an irradiation of a patient, the method comprising:
    acquiring CT measurement data of the patient via a CT device having a quantum counting X-ray detector;
    processing the CT measurement data to generate result data suitable for the planning of the irradiation of the patient, wherein
        the processing of the CT measurement data is based on an information content of the CT measurement data resulting from use of the quantum counting X-ray detector in the acquiring of the CT measurement data; and
    provisioning the result data to an interface for planning the irradiation of the patient,
    wherein the acquiring of the CT measurement data of the patient includes:
        changing a detector parameter of the quantum counting X-ray detector during the acquiring of the CT measurement data, wherein
        the changing of the detector parameter includes changing the detector parameter of the quantum counting X-ray detector during the acquiring of the CT measurement data such that a first setting of the detector parameter is set for acquiring the CT measurement data of a first body region of the patient, and a second setting of the detector parameter is set for acquiring the CT measurement data of a second body region of the patient.

11. The method as claimed in claim 10, further comprising:
   establishing the first body region and the second body region using at least one of existing medical image data of the patient or an Atlas database.

12. The method as claimed in claim 10, wherein
   the first body region includes a target volume of the irradiation, and
   the second body region includes a body region outside the target volume of the irradiation.

13. The method as claimed in claim 10, wherein
   the first body region is a region of the patient positioned in a beam region during the irradiation of the patient, and
   the second body region is a region of the patient positioned outside the beam region during the irradiation of the patient.

14. The method as claimed in claim 10, wherein the first body region receives a higher radiation dose than the second body region during the irradiation of the patient.

15. The method as claimed in claim 10, wherein
   the changing of the detector parameter includes changing the detector parameter of the quantum counting X-ray detector during the acquiring of the CT measurement data such that a higher resolution of the quantum counting X-ray detector is set for the acquiring of the CT measurement data from the first body region of the patient than for the acquiring of the CT measurement data from the second body region of the patient.

16. A method for provisioning result data suitable for planning an irradiation of a patient, the method comprising:
   acquiring CT measurement data of the patient via a CT device having a quantum counting X-ray detector the acquiring including changing a detector parameter of the quantum counting X-ray detector during the acquiring, the changing the detector parameter including changing the detector parameter of the quantum counting X-ray detector during the acquiring of the CT measurement data such that a first setting of the detector parameter is set for acquiring the CT measurement data in a first rotational position of a detector-emitter system of the CT device, and a second setting of the detector parameter is set for acquiring the CT measurement data in a second rotational position of the detector-emitter system of the CT device;
   processing the CT measurement data to generate result data suitable for the planning the irradiation of the patient, the processing the CT measurement data based on an information content of the CT measurement data resulting from use of the quantum counting X-ray detector in the acquiring of the CT measurement data; and
   provisioning the result data to an interface for planning the irradiation of the patient.

* * * * *